United States Patent
Benson et al.

[11] Patent Number: 5,840,999
[45] Date of Patent: Nov. 24, 1998

[54] ASYMMETRIC BENZOXANTHENE DYES

[75] Inventors: Scott C. Benson, Oakland; Steven M. Menchen, Fremont; Peter D. Theisen, South San Francisco; Kevin M. Hennessey; Vergine C. Furniss, both of San Mateo; Joan Hauser, Oakland, all of Calif.

[73] Assignee: The Perkin-Elmer Corporation, Foster City, Calif.

[21] Appl. No.: 824,102

[22] Filed: Mar. 26, 1997

Related U.S. Application Data

[62] Division of Ser. No. 626,085, Apr. 1, 1996.
[51] Int. Cl.$^6$ .............................. C07C 39/14; C07C 37/68
[52] U.S. Cl. ........................ 568/735; 568/737; 568/753; 568/757
[58] Field of Search .................................... 568/735, 737, 568/753, 757

[56] References Cited

U.S. PATENT DOCUMENTS 3,997,561  12/1976  Seki et al. ............................... 260/335

(List continued on next page.)

FOREIGN PATENT DOCUMENTS 0 061 746  6/1982  European Pat. Off. ........ C07H 19/04

(List continued on next page.)

OTHER PUBLICATIONS

Bisanz et al., "Orientation in the Friedel–Crafts Acylation of α– and β–naphthol Derivatives. II. Reactions of 2–methyl-naphthoresorcinol with Benzoyl Chloride Without a Catalyst and in the Presence of ZnCl2," *Rocz. Chem.* 41(5):803–814, Politech. Warszawa, Warsaw, Poland, Coden:Rochac, Journal written in Polish, Can 69:96313 (Abstract Only).

(List continued on next page.)

*Primary Examiner*—Ardin H. Marschel
*Assistant Examiner*—Jezia Riley
*Attorney, Agent, or Firm*—Paul D. Grossman

[57] ABSTRACT

A class of asymmetric monobenzoxanthene compounds useful as fluorescent dyes are disclosed having the structure

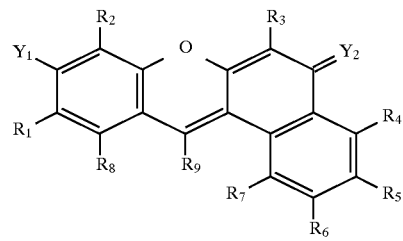

wherein $Y_1$, and $Y_2$ are individually hydroxyl, amino, imminium, or oxygen, $R_1$–$R_8$ are hydrogen, fluorine, chlorine, alkyl alkene, alkyne, sulfonate, amino, amido, nitrile, alkoxy, linking group, and combinations thereof, and $R_9$ is acetylene, alkane, alkene, cyano, substituted phenyl and combinations thereof The invention ftrther includes novel intermediate compounds useful for the synthesis of asymmetric benzoxanthene compounds having the general structure

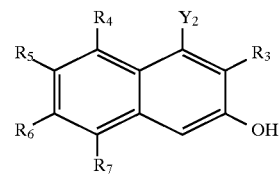

where substituents $R_3$–$R_7$ correspond to like-referenced substituents in the structure of described above, and $Y_2$ is hydroxyl or amine. In another aspect, the invention includes methods for synthesizing the above dye compounds and intermediates. In yet another aspect, the present invention includes reagents labeled with the asymmetric benzoxanthene dye compounds, including deoxynucleotides, dideoxynucleotides, phosphoramidites, and polynucleotides. In an additional aspect, the invention includes methods utilizing such dye compounds and reagents including dideoxy polynucleotide sequencing and fragment analysis methods.

5 Claims, 13 Drawing Sheets

U.S. PATENT DOCUMENTS

| | | | |
|---|---|---|---|
| 4,318,846 | 3/1982 | Khanna et al. | 530/391.5 |
| 4,757,141 | 7/1988 | Fung et al. | 536/27 |
| 4,933,471 | 6/1990 | Lee | 549/33 |
| 4,945,171 | 7/1990 | Haugland et al. | 549/224 |
| 5,066,580 | 11/1991 | Lee | 435/7.21 |
| 5,093,232 | 3/1992 | Urdea et al. | 435/6 |
| 5,188,934 | 2/1993 | Menchen et al. | 435/6 |
| 5,212,304 | 5/1993 | Fung et al. | 544/157 |
| 5,231,191 | 7/1993 | Woo et al. | 549/220 |
| 5,366,860 | 11/1994 | Bergot et al. | 435/6 |

FOREIGN PATENT DOCUMENTS

| | | | |
|---|---|---|---|
| 0 233 053 | 8/1987 | European Pat. Off. | C12Q 1/68 |
| 0 251 786 | 1/1988 | European Pat. Off. | C07D 403/04 |
| 0 252 683 | 1/1988 | European Pat. Off. | C07H 21/04 |
| 0 617 047 | 9/1994 | European Pat. Off. | C07H 21/00 |
| 2 556 726 | 12/1984 | France | C07H 21/00 |
| 84 990 C | 2/1895 | Germany . | |
| 290 508 C | 6/1915 | Germany . | |
| WO 91/05060 | 4/1991 | WIPO . | |
| WO 91/07507 | 5/1991 | WIPO | C12Q 1/68 |
| WO 94/05688 | 3/1994 | WIPO | C07H 21/00 |

OTHER PUBLICATIONS

Crossfire Database, Beilstein Informationssysteme Gmbh, brn=3501684, XP002037261, excerpt from Inoue et al., "Yuki Gosel Kagaku Kyokaaishi," *Journal* 17:714 Osaka, Japan (1959).

Masao et al., "Absorption and Fluorescence Spectra of Halogen Derivatives of Fluorescein," *Chemical Abstracts* 77(12):84 (Sep. 18, 1972) Abstract 76642w.

Setsuko et al., "Application of the Polyamide Chromatography to the Separation of Fluorescein Dyes," *Chemical Abstracts* 77(18):86 (Oct. 30, 1972) Abstract 116016d.

Lee et al., "Vita Blue: A New 633–nm Excitable Fluorescent Dye for Cell Analysis," *Cytometry* 10(2):151–164 (Mar., 1989).

Fluka, Chemika–Biochemika Catalog, CH–9470 Buchs/Switzerland, p. 942, 1993.

The Merck Index, Eleventh Edition, Published By Merck & Co., Inc., Rahway, NJ p. 1012, 1989.

22

23

R = H 24
R = Cl 25

26

ASYMMETRIC BENZOXANTHENE DYES

This is a divisional of co-pending application Ser. No. 08/626,085 filed on Apr. 1, 1996, which application is incorporated herein by reference and to which application priority is claimed under 35 USC §120.

FIELD OF THE INVENTION

This invention relates generally to fluorescent dye compounds useful as molecular probes. More specifically, this invention relates to asymmetric benzoxanthene dyes useful as fluorescent labeling reagents.

BACKGROUND

The non-radioactive detection of biological analytes is an important technology in modern analytical biotechnology. By eliminating the need for radioactive labels, safety is enhanced and the environmental impact of reagent disposal is greatly reduced, resulting in decreased costs for analysis. Examples of methods utilizing such non-radioactive detection methods include DNA sequencing, oligonucleotide probe methods, detection of polymerase-chain-reaction products, immunoassays, and the like.

In many applications the independent detection of multiple spatially overlapping analytes in a mixture is required, e.g., single-tube multiplex DNA probe assays, immuno assays, multicolor DNA sequencing methods, and the like. In the case of multi-loci DNA probe assays, by providing multicolor detection, the number of reaction tubes may be reduced thereby simplifying the experimental protocols and facilitating the manufacturing of application-specific kits. In the case of automated DNA sequencing, multicolor labeling allows for the analysis of all four bases in a single lane thereby increasing throughput over single-color methods and eliminating uncertainties associated with inter-lane electrophoretic mobility variations.

Multiplex detection imposes a number of severe constraints on the selection of dye labels, particularly for analyses requiring an electrophoretic separation and treatment with enzymes, e.g., DNA sequencing. First, it is difficult to find a collection of dyes whose emission spectra are spectrally resolved, since the typical emission band half-width for organic fluorescent dyes is about 40–80 nanometers (nm) and the width of the available spectrum is limited by the excitation light source. As used herein the term "spectral resolution" in reference to a set of dyes means that the fluorescent emission bands of the dyes are sufficiently distinct, i.e., sufficiently non-overlapping, that reagents to which the respective dyes are attached, e.g. polynucleotides, can be distinguished on the basis of the fluorescent signal generated by the respective dyes using standard photodetection systems, e.g. employing a system of band pass filters and photomultiplier tubes, charged-coupled devices and spectrographs, or the like, as exemplified by the systems described in U.S. Pat. Nos. 4,230,558, 4,811,218, or in Wheeless et al, pgs. 21–76, in *Flow Cytometry: Instmumentation and Data Analysis* (Academic Press, New York, 1985). Second, even if dyes with non-overlapping emission spectra are found, the set may still not be suitable if the respective fluorescent efficiencies are too low. For example, in the case of DNA sequencing, increased sample loading can not compensate for low fluorescence efficiencies, Pringle et al., DNA *Core Facilities Newsletter*, 1: 15–21 (1988). Third, when several fluorescent dyes are used concurrently, simultaneous excitation becomes difficult because the absorption bands of the dyes are widely separated. Fourth, the charge, molecular size, and conformation of the dyes must not adversely affect the electrophoretic mobilities of the fragments. Finally, the fluorescent dyes must be compatible with the chemistry used to create or manipulate the fragments, e.g., DNA synthesis solvents and reagents, buffers, polymerase enzymes, ligase enzymes, and the like.

Because of these severe constraints only a few sets of fluorescent dyes have been found that can be used in multicolor applications, particularly in the area of four-color DNA sequencing, e.g., Smith et al., *Nucleic Acids Research*, 113; 2399–2412 (1985); Prober et al., *Science*, 238: 336–341 (1987); and Connell et al., *Biotechniques*, 5: 342–348 (1987). FIG. 1 shows examples of fluorescent xanthene dyes currently used as long-wavelength labels emitting above 550 nm including the two rhodamine-based dyes TAMRA (22) and ROX (26) and the two fluorescein-based dyes HEX (23) and NAN (24).

SUMMARY

The present invention is directed towards our discovery of a class of asymmetric benzoxanthene dyes useful as fluorescent dyes.

It is an object of our invention to provide a class of asymmetric benzoxanthene dyes useful for the simultaneous detection of multiple spatially-overlapping analytes which satisfies the constraints described above and provide fluorescence emission maxima above 550 nm when illuminated by excitation light having a wavelength of between 480 nm and 550 nm.

It is a firther object of our invention to provide a class of asymmetric benzoxanthene dyes useful for the simultaneous detection of multiple spatially-overlapping analytes which satisfies the constraints described above and whose fluorescence properties may be tuned by manipulation of substituents at a variety of positions.

It is another object of our invention to provide methods and intermediate compounds useful for the synthesis of the asymmetric benzoxanthene dyes of our invention.

It is a further object of our invention to provide nucleotides and polynucleotides labeled with the ayymmetric benzoxanthene dyes of our invention.

It is another object of our invention to provide phosphoramidite compounds including the asymmetric benzoxanthene dyes of our invention.

It is another object of our invention to provide fragment analysis methods, including DNA sequencing methods, employing the asymmetric benzoxanthene dyes of our invention.

In a first aspect, the foregoing and other objects of our invention are achieved by an asymmetric benzoxanthene dye compound having the formula:

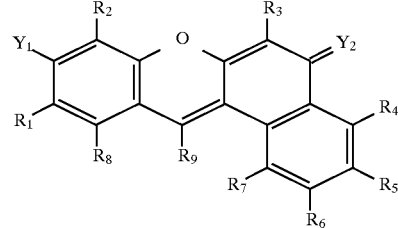

wherein $Y_1$ and $Y_2$ taken separately are hydroxyl, oxygen, imminium, or amine. $R_1$–$R_8$ taken separately are hydrogen, fluorine, chlorine, lower allyl, lower alkene, lower alkyne, sulfonate, amino, ammonium, amido, nitrile, alkoxy, linking group, or combinations thereof. And, $R_9$ is acetylene, alkane, alkene, cyano, substituted phenyl, or combinations thereon the substituted phenyl having the structure:

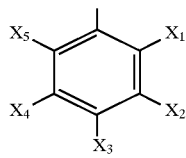

wherein $X_1$ is carboxylic acid or sulfonic acid; $X_2$ and $X_5$ taken separately are hydrogen, chlorine, fluorine, or lower alkyl; and $X_3$ and $X_4$ taken separately are hydrogen, chlorine, fluorine, lower alkyl, carboxylic acid, sulfonic acid, or linking group.

In a second aspect, the invention includes phosphararidite compounds having the formula:

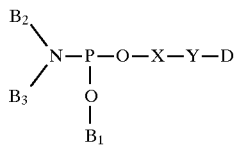

wherein X is a spacer arm; Y is a linkage; $B_1$ is a phosphite ester protecting group; $B_2$, and $B_3$ taken separately are selected from the group consisting of lower alkyl, lower alkene, lower aryl having between 1 and 8 carbon atoms, arylalkyl, and cycloalkyl containing up to 10 carbon atoms; and D is the asymmetric benzoxanthene dye compound described above. Y and D are linked through a linkage formed by the reaction of a linking group and its complementary functionality, such linkage being attached to dye D at one of positions $R_1$–$R_9$.

In a third aspect, the invention includes a phosphoramidite compound having the formula:

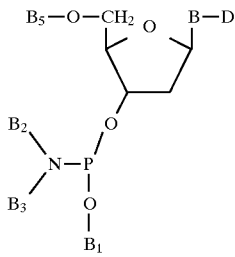

wherein $B_1$ is a phosphite ester protecting group, $B_2$ and $B_3$ taken separately are selected from the group consisting of lower alkyl, lower alkene, lower aryl having between 1 and 8 carbon atoms, arylalkyl and cycloalkyl containing up to 10 carbon atoms; $B_5$ is an acid-cleavable hydroxyl protecting group; B is a nucleotide base; and D is the dye compound described above. When B is purine or 7-deazapurine, the sugar moiety is attached at the $N^9$-position of the purine or 7-deazapurine, and when B is pyrimidine, the sugar moiety is attached at the $N^1$-position of the pyrimidine. B and D are linked through a linkage formed by the reaction of a linking group and its complementary functionality, such linkage being attached to D at one of positions R-position of the purine, if B is 7-deazapurine, the linkage is attached to the 7-position of the 7-deazapurine, and if B is pyrimidine, the linkage is attached to the 5-position of the pyrimidine. Preferably B is selected from the group consisting of uracil, cytosine, 7-deazaadenine, and 7-deazaguanosine.

In a fourth aspect, the present invention includes a compound useful as an intermediate in the synthesis of the above described asymmetric benzoxanthene dyes, such compound having the formula:

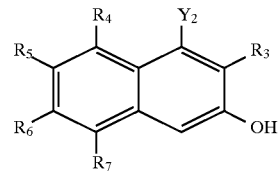

wherein $R_3$–$R_7$ are as described above and $Y_2$ is hydroxyl or amine. In a particularly preferred embodiment of this aspect, $R_3$ is fluorine and $Y_2$ is hydroxyl.

In a fifth aspect, the invention includes a nucleotide labeled with the above described asymmetric benzoxanthene dyes of the invention, the nucleotide having the formula:

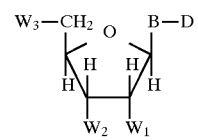

wherein B is a 7-deazapurine, purine, or pyrimidine nucleotide base; $W_1$ and $W_2$ taken separately are H or OH; $W_3$ is OH,

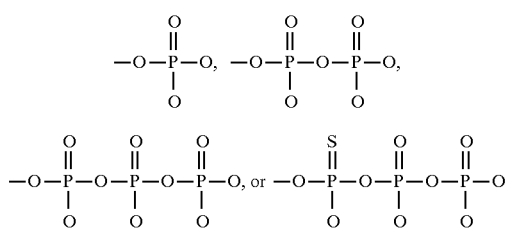

and, D is a dye compound of the invention. When B is purine or 7-deazapurine, the sugar moiety is attached at the $N^9$-position of the purine or deazapurine, and when B is pyrimidine, the sugar moiety is attached at the $N^1$-position of the pyrimidine. The linkage linking B and D is attached to D at one of positions $R_1$–$R_9$. If B is a purine, the liage is attached to the 8-position of the purine, if B is 7-deazapurine, the linkage is attached to the 7-position of the 7-deamapurine, and if B is pyrimidine, the linkage is attached to the 5-position of the pyrimidine. Preferably B is selected from the group consisting of uracil, cytosine, deazaadenine, and deaaaguanosine.

In a sixth aspect, the invention includes labeled polynucleotides containing a nucleotide having the formula:

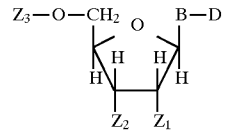

wherein B is a 7-deazapurine, purine, or pyrimidine nucleotide base; $Z_1$ is H or OH; $Z_2$ is H, OH, $HPO_4$, and Nuc, wherein "Nuc" refers to a nucleotide. The nucleoside and Nuc are linked by a phosphodiester linkage, the linkage being attached to the 5'-position of Nuc; $Z_3$ is selected from the group consisting of H, $HPO_3$ and phosphate analogs thereof, and Nuc, wherein Nuc and the nucleoside are linked by a phosphodiester linkage, the linkage being attached to the 3'-position of Nuc; and D is a dye compound of the invention. Phosphate analogs of $HPO_3$ include analogs wherein a non-bridging oxygen is replaced by a non-oxygen moiety, e.g., sulphur, arnino, anilidate, anilinthioate, and the like.

When B is purine or 7-deazapurine, the sugar moiety is attached at the $N^9$-position of the purine or deazapurine, and when B is pyrimidine, the sugar moiety is attached at the $N^1$-position of the pyrimidine. The linkage linking B and D is attached to D at one of positions $R_1-R_9$. If B is a purine, the linkage is attached to the 8-position of the purine, if B is 7-deazapurine, the linkage is attached to the 7-position of the 7-deazapurine, and if B is pyrimidine, the linkage is attached to the 5-position of the pyrimidine. Preferably B is selected from the group consisting of uracil, cytosine, deazaadenine, and deazaguanosine.

In a seventh aspect, the invention includes a method of polynucleotide sequencing using the dyes of the invention. The method comprises the steps of forming a mixture of a first, a second, a third, and a forth class of polynucleotides such that each polynucleotide in the first class includes a 3'-terminal dideoxyadenosine and is labeled with a first dye; each polynucleotide in the second class includes a 3'-terminal dideoxycytidine and is labeled with a second dye; each polynucleotide in the third class includes a 3'-terminal dideoxyguanosine and is labeled with a third dye; and each polynucleotide in the forth class includes a 3'-terminal dideoxythymidine and is labeled with a forth dye. In the method, one or more of the first, second, third, or forth dyes is an asymmetric benzoxanthene dye of the invention. The other of the dyes is chosen such that they are spectrally resolvable from the asymmetric benzoxanthene dye(s) and from each other. After forming the above mixture, the polynucleotides are electrophoretically separated thereby forming bands of similarly sized polynucleotides. Next, the bands are illuminated with an illumination beam capable of causing the dyes to fluoresce. Finally, the classes of the polynucleotides are identified by the fluorescence spectrum of the labeled polynucleotides in each band.

In an eighth aspect, the invention includes a method of fragment analysis utilizing the dye compounds of the present invention. The method of this aspect comprises the steps of: forming a labeled polynucleotide fragment, the fragment being labeled with a dye compound of the invention; subjecting the labeled polynucleotide fragment to a size-dependent separation process; and detecting the labeled polynucleotide fragment subsequent to the separation process.

The dyes of the present invention provide at least seven important advantages over currently available dyes used for the simultaneous detection of multiple spatially-overlapping analytes, particularly in the area of multicolor fluorescence-based DNA sequencing. First, the dyes of the present invention are much more stable to DNA synthesis conditions then are presently available dyes having the desired spectral characteristics. This enhanced stability to DNA synthesis conditions makes it possible to more readily prepare labeled oligonucleotide reagents using automated DNA synthesis technologies, e.g., labeled PCR primers, DNA sequencing primers, and oligonucleotide hybridization probes. Second, the dyes of the present invention are significantly more photostable than fluorescein-based dyes previously employed in the wavelength region above about 550 nm. Third, the dyes of the present invention have an absorption spectrum which has a blue "shoulder" thereby permitting more efficient excitation of the dyes at shorter wavelengths than dibenzoxanthene dyes or rhodamine-based dyes. Fourth, the asymmetric benzoxanthene dyes of the present invention have significantly higher quantum yields then do spectrally similar rhodamine-based dyes. Fifth, the enhanced excitation efficiency with typical light sources coupled with the high quantum yields of the dyes of the present invention make the dyes significantly brighter than presently available dyes having the desired spectral characteristics. Brightness is particularly important in the context of DNA sequencing applications where the amount of analyte is limited by electrophoresis loading factors and the total fluorescence is distributed over hundreds of spatially separated species. As used herein the term "brightness" refers to the combined effects of extinction coefficient and fluorescence quantum yield on ultimate fluorescence emission intensity. By increasing the brightness of the fluorescent labels, the larger, less abundant fragments can be more readily detected and less sample need be loaded into the electrophoresis, thereby resulting in superior electrophoretic resolution. Moreover, the increased brightness of the analytes contributes to increased signal-to-noise ratio leading to improved deconvolution of spatially and spectrally neighboring species. Sixth, the asymmetry of the dyes of the present invention permits tuning of the emission spectrum of the dyes by varying the substituents $R_1-R_9$, particularly substituents $R_1-R_3$ on the resorcinol-derived portion of the dye. Only one equivalent substituent position is available on symmetric dibenzoxanthene compounds, thereby greatly limiting the degrees of freedom available for spectral tuning of the dyes. Seventh, the dyes of the invention are readily converted to stable phosphoramidite derivatives which can be employed in the automated chemical synthesis of labeled oligonucleotides.

These and other objects, features, and advantages of the present invention will become better understood with reference to the following description, drawings, and appended claims.

DETAILED DESCRIPTION OF THE PREFERRED EMBODIMENTS

Figure 1:
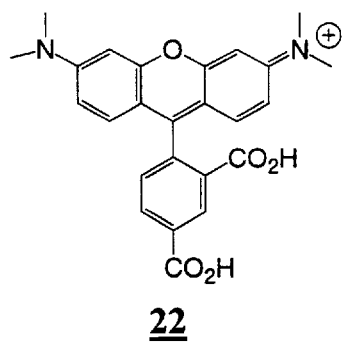
FIG. 1 shows the structures of various fluorescent dyes previously employed as long-wavelength labels, i.e., labels emitting above 550 nm.
Figure 1:
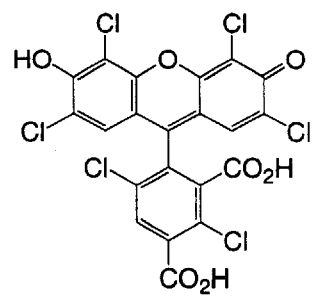
Figure 1:
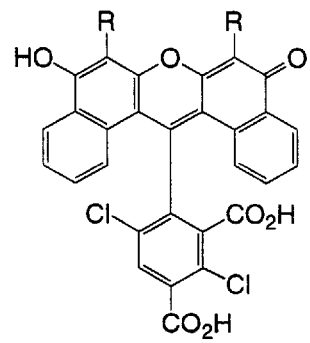
Figure 1:
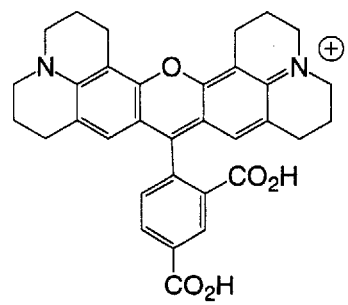

Reference will now be made in detail to certain preferred embodiments of the invention. While the invention will be described in conjunction with the preferred embodiments, it will be understood that they are not intended to limit the invention to those embodiments. On the contrary, the invention is intended to cover alternatives, modifications, and equivalents, which may be included within the invention as defined by the appended claims.

Generally, the present invention comprises a novel class of asymmetric benzoxanthene compounds useful as fluorescent dyes, methods and intermediates for synthesis of such dyes, reagents employing such dyes as molecular labels, and methods utilizing such dyes and reagents in the area of analytical biotechnology. The compounds of the present invention find particular application in the area of multicolor fluorescent DNA sequencing and fragment analysis.

I. Asymmetric Benzoxanthene Dye Compounds

In a first aspect, the present invention comprises a novel class of asymmetric benzoxanthene dye compounds having the general structure shown in Formula I immediately below. (AU molecular structures provided herein are intended to encompass not only the exact electronic structure presented, but also include all resonant structures and protonation states thereof)

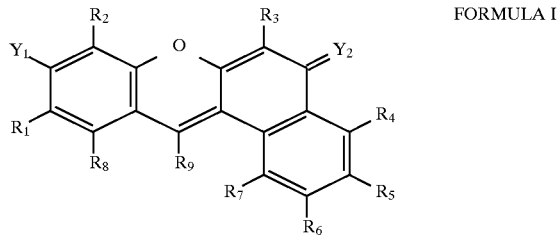

FORMULA I

In Formula I, $Y_1$ and $Y_2$ are either individually hydroxyl, oxygen, amine, imminium or oxygen. When $Y_1$ is hydroxyl and $Y_2$ is oxygen, the compound is analogous to fluorescein, while when $Y_1$ is amine and $Y_2$ is inmminiurn, the compound is analogous to rhodamnine. Preferably $Y_1$ is hydroxyl and $Y_2$ is oxygen.

Moieties $R_1$–$R_9$ are substituents used to modulate various properties of the dyes by modifying the electronic structure of the ground and excited states of the molecule. In particular, varying moieties $R_1$–$R_9$ affects the spectral characteristics, chemical stability, and photostability of the compounds. Substituents $R_1$–$R_3$ and $R_9$ are particularly important in defning the properties of the compounds of Formula I. For example, it has been observed that placing a fluorine atom at one of positions $R_1$–$R_3$ leads to increased chemical and photostability, and that if $R_9$ is substituted phenyl, making substituents $X_2$ and $X_5$ chlorine leads to narrower emission bands. (See below for the definition of substituents $X_2$ and $X_5$.)

Preferably, substituents $R_1$–$R_8$ are hydrogen, fluorine, chlorine, lower allkyl, lower alkene, lower allyne, sulfonate, sulfone, amino, imminiium, amido, nitrile, aryl, lower alkoxy, linking group, or combinations thereof where as used herein the term "linking group" refers to a functionality capable of reacting with a "complementary functionality" attached to a reagent, such reaction forming a "linkage" connecting the dye to the reagent. More will be said about particular linking groups, complementary functionalities, and linkages in a subsequent section of this disclosure. Preferably, $R_1$ is lower alkoxy, chlorine, fluorine, or hydrogen; $R_2$ is lower alkyl, fluorine, or chlorine; and $R_3$ is lower alkyl, or fluorine. More preferably, one of $R_1$, $R_2$, and $R_3$ is fluorine. In a particularly preferred embodiment, at least $R_3$ is fluorine.

As used herein, the term "lower alkyl" denotes straight-chain and branched hydrocarbon moieties containing from 1 to 8 carbon atoms, i.e., methyl, ethyl, propyl, isopropyl, tert-butyl isobutyl, sec-butyl, neopentyl, tert-pentyl, and the like. "Lower substitued alkyl" denotes a lower alkyl including electron-withdrawing substituents, such as halo, cyano, nitro, sulfo, or the like. "Lower haloalkyl" denotes a lower substituted alkyl with one or more halogen atom substituents, usually fluoro, chloro, bromo, or iodo. "Lower alkene" denotes a hydocarbon containing from 1 to 8 carbon atoms wherein one or more of the carbon-carbon bonds are double bonds, wherein the non-double bonded carbons comprise lower alkyl or lower substituted alkyl. "Lower alkyne" denotes a hydocarbon containing from 1 to 8 carbon atoms wherein one or more of the carbons are bonded with a triple bond, wherein the non-triple bonded carbons comprise lower alkyl or lower substituted alky. "Sulfonate" refers to moieties including a sulfiur atom bonded to 3 oxygen atoms, including mono- and di-salts thereof, e.g., sodium sulfonate, potassium sulfonate, disodium sulfonate, and the like. "Amino" refers to moieties including a nitrogen atom bonded to 2 hydrogen atoms, lower alkyl moieties, or any combination thereof "Amido" refers to moieties including a carbon atom double bonded to an oxygen atom and single bonded to an amino moiety. "Nitrile" refers to moieties including a carbon atom triple bonded to a nitrogen atom. "Lower Alkoxy" refers to a moiety including lower alkyl single bonded to an oxygen atom. "Aryl" refers to single or multiple phenyl or substituted phenyl, e.g., benzene, naphthalene, anthracene, biphenyl, and the like.

Preferably $R_9$ is acetylene, lower alkyl, lower alkene, cyano, phenyl or substituted phenyl, heterocyclic aromatic, or combinations thereof, the substituted phenyl having the structure:

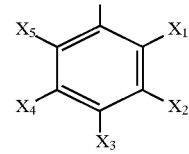

wherein $X_1$–$X_5$ taken separately are hydrogen, chlorine, fluorine, lower alkyl carboxylic acid, sulfonic acid, —$CH_2OH$, or linking group. As used herein, the term "heterocyclic aromatic" refers to aromatic moieties having a heteroatom as part of the cyclic structure, e.g., pyrole, furan, indole, and the like. Preferably, $X_1$ is carboxylic acid, sulfonic acid, or —$CH_2OH$; $X_2$ and $X_5$ taken separately are hydrogen, chlorine, fluorine, or lower alkyl and $X_3$ and $X_4$ taken separately are hydrogen, chlorine, fluorine, lower alkyl, carboxylic acid, sulfonic acid, or linking group. More preferably, $X_2$ and $X_5$ are chlorine. In an additional preferred embodiment, one of $X_3$ or $X_4$ is linking group. Preferably, $X_1$ is carboxylic acid. In an additional preferred embodiment particularly suited to forming phosphorarnidite compounds including the dye compound of the invention, one of $X_1$ or $X_5$ is a moiety which is capable of forming a cyclic ester or cyclic ether, e.g., carboxylic acid, sulfonic acid, or —CH₂OH, or any other group that will form a spirocyclic system, i.e., bicyclic compounds having one carbon atom common to both rings, e.g., spiro[4.5]decane.

Preferably the linking group of the invention is isothiocyanate, sulfonyl chloride, 4,6-dichlorotriazinylarnine, succinimidyl ester, or other active carboxylate whenever the complementary functionality is amine. Preferably the linking group is maleimide, halo acetyl or iodoacetamide whenever the complementary functionality is sulfhydryl. See R Haugland, *Molecular Probes Handbook of Fluorescent Probes and Research Chemicals,* Molecular probes, Inc. (1992). In a particularly preferred embodiment, the linking group is an activated N-hydroxysuccinimidyl (NHS) ester which reacts with an amine complementary functionality, where to form the activated NHS ester, a dye of the invention including a carboxylate linking group is reacted with dicyclohexylcarbodiimide and N-hydroxysuccinimide to form the NHS ester. See FIG. 3.

Several alternative generalized methods may be used to synthesize the asymmetric benzoxanthene dye compounds of the present invention, four of which will be described here with reference to FIG. 11. In a first preferred method referred to in FIG. 11 as Route A, compound 27 is reacted with 1,3-dihydroxy or 1,3-aminohydroxy benzene derivative 28 and 1,3-dihydroxy or 1,3-aminohydroxy naphthalene derivative 29 employing equal equivalents of each under acid catalysis and heat to give asymmetric dye compound 30. Preferably compound 27 is a cyclic or straight chain anhydride, e.g., LVG is OCOR₉; ester, e.g., where LVG is OR where R is lower alkyl, phenyl, or sulfonate; or acid chloride, e.g., where LVG is chlorine or other halogen.

Figure 11:
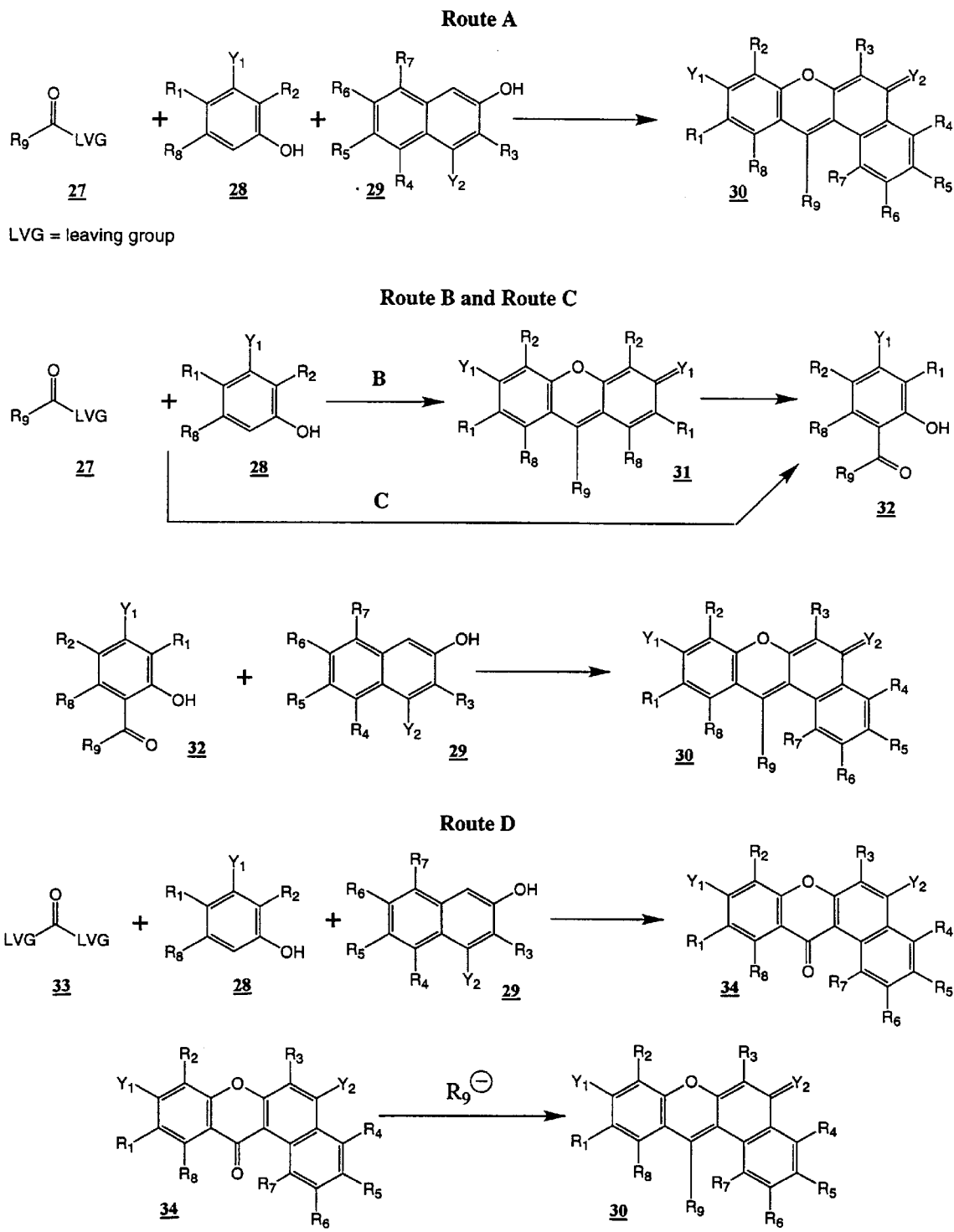
FIG. 11 shows four preferred synthesis routes for the synthesis of the asymmetric benzoxanthene dyes of the invention.

In an alternative preferred synthesis method referred to as Route B in FIG. 11, compound 27 is reacted with 2 equivalents of a 1,3-dihydroxybenzene derivative, i.e., Y₁ is hydroxy, or a 1,3-aminohydroxybenzene derivative, i.e., Y₁ is amino, 28 to give symmetric xanthene dye 31. Compound 31 is then decomposed by base hydrolysis to form intermediate benzoyl condensation product 32. Condensation product 32 is then reacted under acid catalysis and heat with compound 29 to give asymmetric dye 30, where 29 is 1,3-dihydroxynaphthalene when Y₂ is hydroxy, or 1,3-aminohydroxynaphthalene when Y₂ is amino.

In yet a third generalized synthesis method, referred to as Route C in FIG. 11, compound 27 is reacted with 1 equivalent of 28 with heat to give intermediate benzoyl condensation product 32. Compound 32 is then reacted with 29 under acid catalysis and heat to give asymmetric dye 30.

In a fourth generalized synthesis method, referred to as Route D in FIG. 11, equal equivalents of compound 33, compound 28, and compound 29 are reacted under acid catalysis and heat to give asymmetric xanthone intermediate 34. Preferably 33 is a carbonate, e.g., LVG is OR where R is preferably lower alkyl or phenyl; or formate, e.g., where LVG is halogen and OR where R is preferably lower alkyl or phenyl. Compound 34 is then reacted with an anionic organometallic R₉ derivative to give the asymmetric dye 30, e.g., R₉Li, R₉MgX where X is halide, e.g., Br, Cl, I, and the like.

Figure 2A:
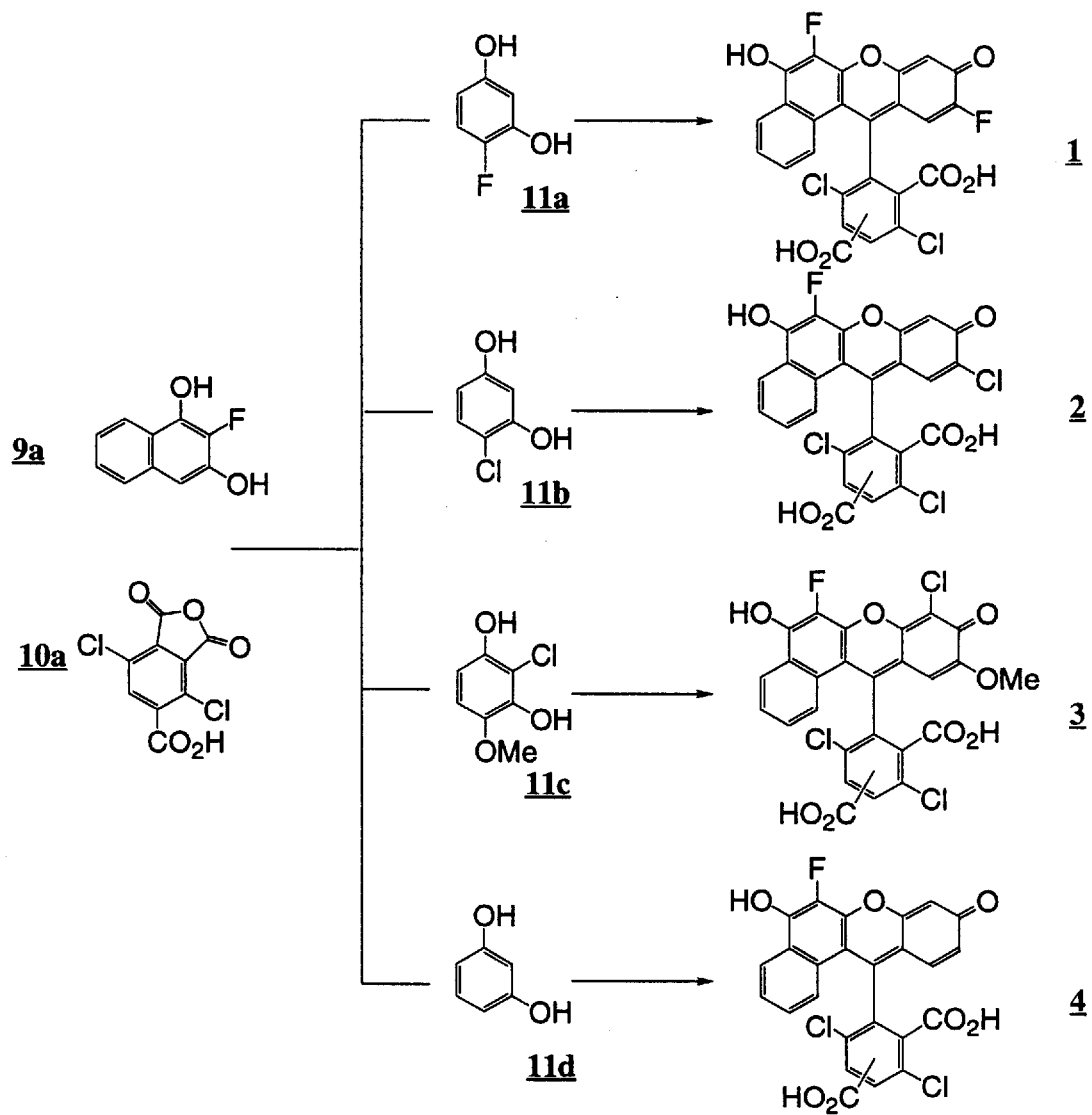
FIGS. 2A and 2B depict a preferred synthesis of the asymmetric benzoxanthene dyes of the invention.
Figure 2B:
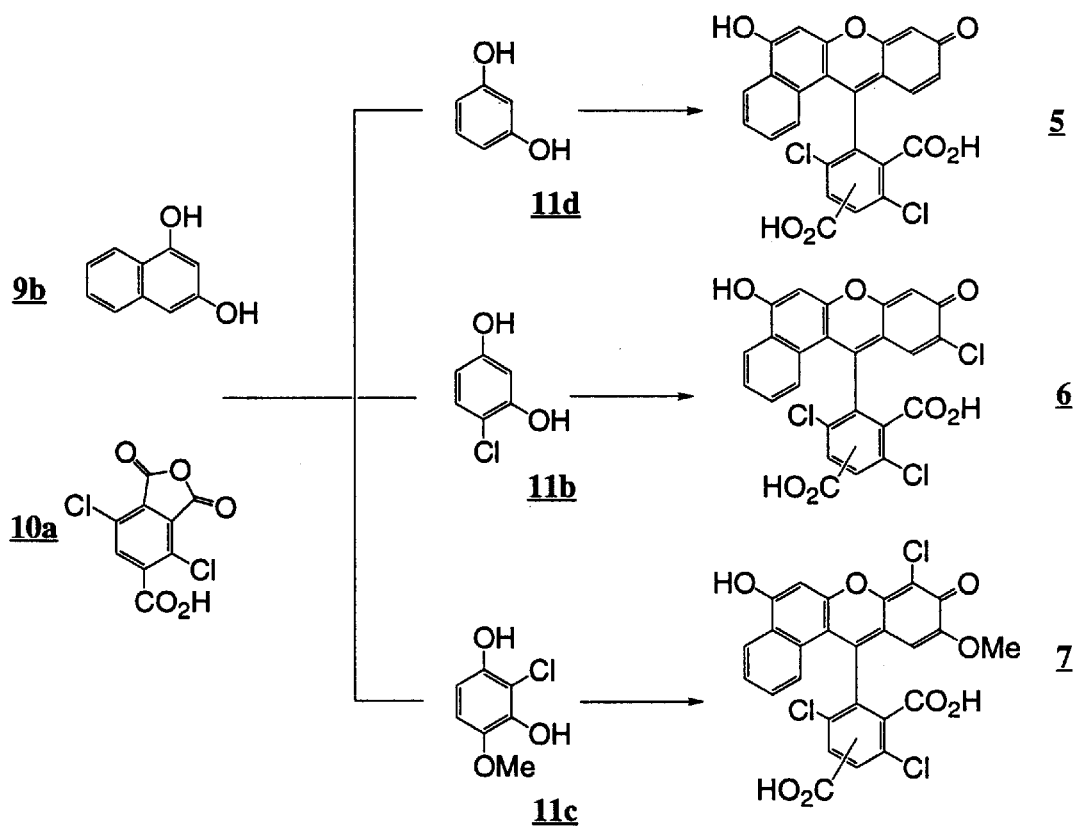

FIGS. 2A and 2B show the synthesis of a set of particularly preferred asymmetric dye compounds of the invention. In this synthesis, a 1,3 dihydroxynapthalene derivative, such as 1,3-dihydroxynapthalene (9b) or 2-fluoro-1,3-dihydroxynapthalene (9a), is reacted with 1 equivalent of a phthallic anhydride derivative, e.g., 3,6-dichlorotrimelletic acid anhydride (10a), and one equivalent of a resorcinol derivative (11a, 11b, 11c, or 11d), and heated for 16 hours in neat organic acid, e.g., MeSO₃H under argon. The crude dye is then precipitated by addition to an ice/water mixture and isolated by filtration. The crude dye is then further purified into 2 isomers 1 and 2 by preparative thin layer chromatography.

Unsubstituted derivatives of the asymmetric benzoxanthene dyes (R₂ and/or R₃ is H) may be reacted further with halogenating reagents, e.g., commercially available sources of positive fluorine, NaOCl, NaOH/Br₂, NaOH/I₂, to produce quantitatively halogenated derivatives, e.g., R₂=R₃=Cl, Br, I, or F after extractive workup with 10% HCl/EtOAc, drying with Na₂SO₄, filtering, and concentrating in vacuo. See inset in FIG. 2B. II. Substituted Naphthalene Intermediates In a second aspect, the present invention comprises novel intermediate compounds useful for the synthesis of the asymmetric benzoxanthene compounds of the subject invention, such intermediate having the general structure shown in Formula II immediately below. In particular, the intermediate compounds of the invention enable the synthesis of asymmetric benzoxanthene compounds with regioselective incorporation of substituents, e.g., halogen atoms, at the 2-position of 2-substituted asymmetric benzoxanthene compounds, where the 2-position corresponds to the R₃ position in the compounds of Formulas I and II.

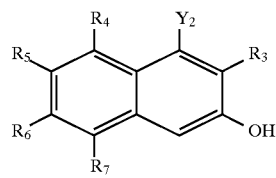

FORMULA II

Substituents R₃–R₇ in the structure of Formula II correspond to like-numbered substituents in the structure of Formula I described above, and Y₂ is hydroxyl or amine. Preferably, R₃ is fluorine and Y₂ is hydroxyl.

Figure 12:
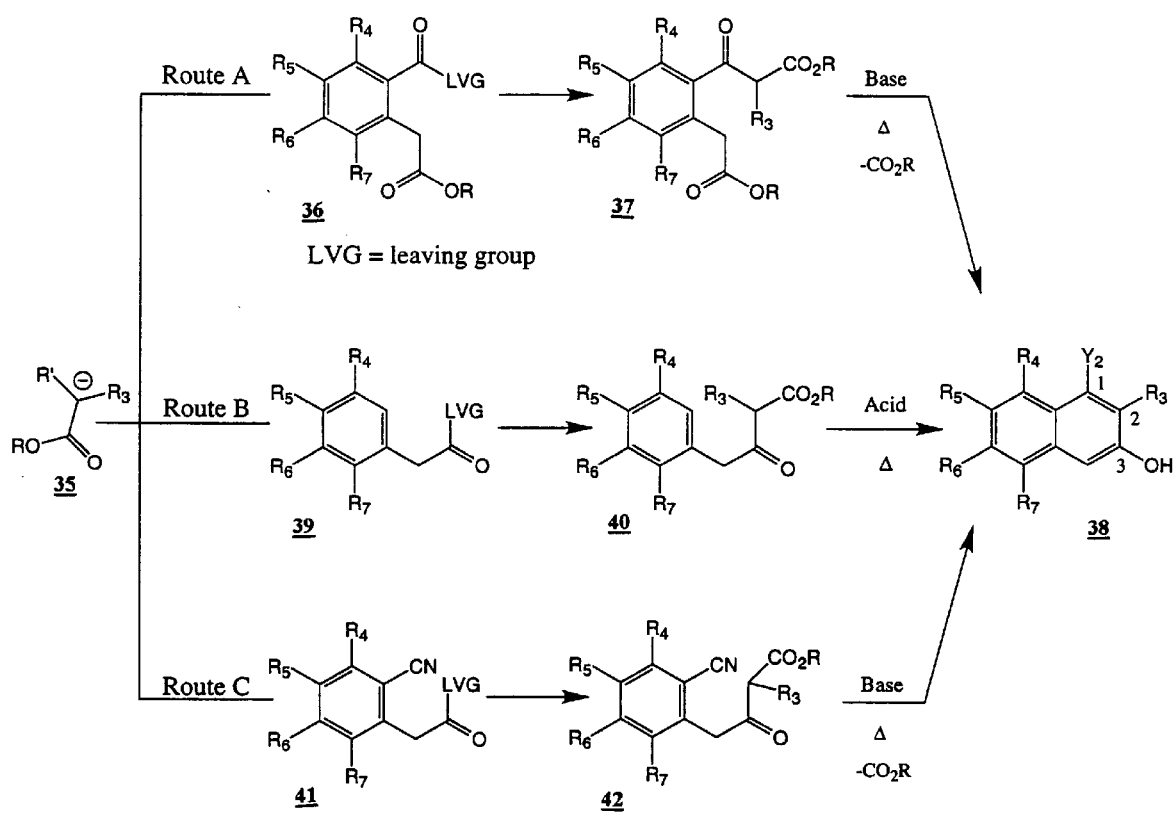
FIG. 12 shows three preferred synthesis routes for the synthesis of the 1-substituted,3-hydroxynapthalene intermediate of the invention.

FIG. 12 shows three alternative generalized synthesis schemes for the synthesis of the substituted naphthalene intermediates of the invention. In a first method indicated as Route A in FIG. 12, substituted ester enolate derivative 35 is reacted with activated homophthallic acid ester derivative 36 to give β-keto-ester derivative 37, e.g., by spontaneous loss of CO₂ when R" is carboxylate. Preferably in compound 35, R" is hydrogen, carboxylate, or halogen and R is lower alkyl. Preferably in compound 36, LVG is halogen, N-hydroxysuccinimide, phenoxide, hydroxybenzotriazole, or carboxylate. Compound 37 is then cyclized under base catalysis and heat to give substituted 1,3-naphthalene diol 38, i.e., Y₂ is OH.

In a second preferred synthesis method indicated as Route B in FIG. 12, compound 35 is reacted with activated phenylacetate derivative 39, where LVG is as described above for compound 36 in Route A, to give , β-keto-ester derivative 40, e.g., by spontaneous loss of CO₂ when R" is carboxylate. Compound 40 is then cyclized under acid catalysis and heat to give substituted 1,3-naphthalene diols 38, i.e., Y₂ is OH.

In a third preferred synthesis method indicated as Route C, compound 35 is reacted with cyano-phenyl acetate derivatives 41, where LVG is as described above for compound 36 in Route A, to give cyano β-keto-ester derivatives 42, e.g., by spontaneous loss of CO₂ when R" is carboxylate. Compound 42 is then cyclized under base catalysis and heat to give substituted 1-amino-3-hydroxynaphthalenes 38, i.e., Y₂ is NH₂.

III. Reagents Utilizing Dye Compounds

In another aspect, the present invention comprises reagents labeled with the asymmetric benzoxanthene dye compounds of Formula I. Reagents of the invention can be virtually anything to which the dyes of the invention can be attached. Preferably the dyes are covalently attached to the reagent. Reagents include proteins, polypeptides, polysaccharides, nucleotides, nucleosides, polynucleotides, lipids, solid supports, organic and inorganic polymers, and combinations and assemblages thereof, such as chromosomes, nuclei, living cells, such as bacteria, other microorganisms, mammalian cells, tissues, and the like.

A. Nucleotide Reagents

A preferred class of reagents of the present invention comprise nucleotides and nucleosides which incorporate the asymmetric benzoxanthene dyes of the invention. Such nucleotide reagents are particularly usefull in the context of labeling polynucleotides formed by enzymatic synthesis, e.g., nucleotide triphosphates used in the context of PCR amplification, Sanger-type polynucleotide sequencing, and nick-translation reactions.

As used herein, "nucleoside" refers to a compound consisting of a purine, deazapurine, or pyrimidine nucleoside base, e.g., adenine, guanine, cytosine, uracil, thymine, deazaadenine, deazaguanosine, and the like, linked to a pentose at the 1' position, including 2'-deoxy and 2'-hydroxyl forms, e.g. as described in Komberg and Baker, *DNA Replication,* 2nd Ed. (Freeman, San Francisco, 1992). The term "nucleotide" as used herein refers to a phosphate ester of a nucleoside, e.g., triphosphate esters, wherein the most common site of esterification is the hydroxyl group attached to the C-5 position of the pentose. "Analogs" in reference to nucleosides include synthetic nucleosides having modified base moieties and/or modified sugar moieties, e.g. described generally by Scheit, *Nucleotide Analogs* (John Wiley, New York, 1980). The term "labeled nucleoside" refers to nucleosides which are covalently attached to the dye compounds of Formula I through a linkage.

Preferred nucleotides of the present invention are shown below in Formula II wherein

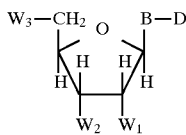

FORMULA III

B is a nucleotide base, e.g., uracii, cytosine, deazaadenine, and deazaguanosine. $W_1$ and $W_2$ taken separately are H or OR $W_3$ is OH,

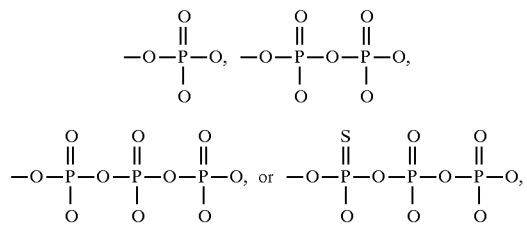

including associated counterions if present, e.g., H, Na, $NH_4$, and the like. D is a dye compound of Formula I. In one particularly preferred embodiment, the nucleotides of the present invention are dideoxynucleotide triphosphates having the structure shown in Formula III.1 below, including associated counterions if present.

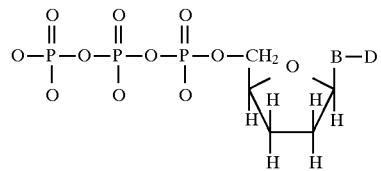

FORMULA III.1

Labeled dideoxy nucleotides such as that shown in Formula III.1 find particular application as chain terminating agents in Sanger-type DNA sequencing methods. In a second particularly preferred embodiment, the nucleotides of the present invention are deoxynucleotide triphosphates having the structure shown in Formula III.2 below, including associated counterions if present.

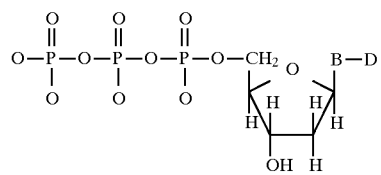

FORMULA III.2

Labeled deoxynucleotides such as that shown in Formula III.2 find particular application as means for labeling polymerase extension products, e.g., in the polymerase chain reaction.

When B is purine or 7-deazapurine, the sugar moiety is attached at the $N^9$-position of the purine or deazapurine, and when B is pyrimidine, the sugar moiety is attached at the $N^1$-position of the pyrimidine.

The linkage linking B and D is attached to D at one of positions $R_1$–$R_9$. Preferably, the linkage is not attached at $R_1$–$R_3$. When the dyes of the invention are synthesized from trimeuletic anhydride, $R_9$ is preferably substituted phenyl and the linkage is attached to the dye at one of the $X_3$ or $X_4$ positions of the substituted phenyl, the other position being a hydrogen atom.

When B is a purine, the linkage linking B and D is attached to the 8-position of the purine, when B is 7-deazapurine, the linkage is attached to the 7-position of the 7-deazapurine, and when B is pyrimdine, the linkage is attached to the 5-position of the pyrimidine.

Nucleoside labeling can be accomplished using any of a large number of known nucleoside labeling techniques using known linkages, linking groups, and associated complementary functionalities. The linkage linking the dye and nucleoside should (i) be stable to oligonucleotide synthesis conditions, (ii) not interfere with oligonucleotide-target hybridization, (iii) be compatible with relevant enzymes, e.g., polymerases, ligases, and the like, and (iv) not quench the fluorescence of the dye.

Preferably, the dyes are covalently linked to the 5-carbon of pyrimidine bases and to the 7-arbon of 7-deazapurine bases. Several suitable base labeling procedures have been reported that can be used with the invention, e.g. Gibson et al, *Nucleic Acids Research,* 15:6455–6467 (1987); Gebeyehu et al, *Nucleic Acids Research,* 15: 4513–4535 (1987); Haralambidis et al, *Nucleic Acids Research,* 15: 4856–4876 (1987); Nelson et al., *Nucleosides and Nucleotides,* 5(3): 233–241 (1986); Bergstrom, et al., *JACS,* 111: 374–375 (1989); U.S. Pat. Nos. 4,855,225, 5,231,191, and 5,449,767. Accordingly, these references are incorporated by reference.

Preferably, the linkages are acetylenic arnido or alkenic amido linkages, the linkage between the dye and the nucleotide base being formed by reacting an activated N-hydroxysuccinlnde (NHS) ester of the dye with an alkynylamino- or alkenylarnino-derivatized base of a nucleotide. More preferably, the resulting linkage is 3-(carboxy) amino-1-propynyl or 3-amino-1-propyn-1-yl (Formula III.3). Several preferred linkages for linking the dyes of the invention to a nucleoside base are shown below in Formulas III.3, III.4, and III.5

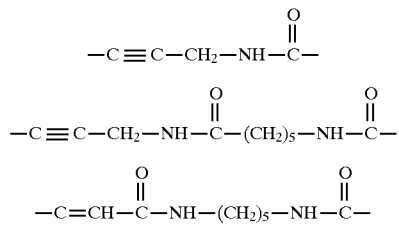

The synthesis of alkynylamino-derivatized nucleosides is taught by Hobbs et al. in European Patent Application No. 87305844.0, and Hobbs et al., *J Org. Chem.*, 54: 3420 (1989), which is incorporated herein by reference. Briefly, the alkynylamino-derivatized nucleotides are formed by placing the appropriate halodideoxynucleoside (usually 5-iodopyrimidine and 7-iodo-7-deazapurine dideoxynucleosides as taught by Hobbs et al. (cited above)) and Cu(I) in a flask, flushing with argon to remove air, adding dry DMF, followed by addition of an alkynylamine, triethyl-amine and Pd(0). The reaction mixture can be strrred for several hours, or until thin layer chromatography indicates consumption of the halodideoxynucleoside. When an unprotected alkynylarnine is used, the alyynylainino-nucleoside can be isolated by concentrating the reaction nixture and chromatographing on silica gel using an eluting solvent which contains ammonium hydroxide to neutralize the hydrohalide generated in the coupling reaction. When a protected aylamine is used, methanol/methylene chloride can be added to the reaction mixture, followed by the bicarbonate form of a strongly basic anion exchange resin. The slurry can then be stirred for about 45 minutes, filtered, and the resin rinsed with additional methanol/methylene chloride. The combined filtrates can be concentrated and purified by flash-chromatography on silica gel using a methanol-methylene chloride gradient. The triphosphates are obtained by standard techniques.

B. Phosphoramidite Reagents Another preferred class of reagents comprise phosphoramidite compounds which incorporate the asymmetric benzoxanthene dyes of the invention. Such phosphoramidite reagents are particularly useful for the automated chemical synthesis of polynucleotides labeled with the asynmmetric benzoxanthene dyes of the invention. Such phosphoramidite compounds when reacted with a 5'-hydroxyl group of a nucleotide or polynucleotide form a phosphite ester linker which, in turn, is oxidized to give a phosphate ester linker, e.g., U.S. Pat. Nos. 4,458,066 and 4,415,732, both patents hereby incorporated by reference.

1. Non-nucleotide Phosphoramidite Reagents: Generally, in one aspect, the phosphoramidite reagents of the invention have the structure of Formula IV immediately below,

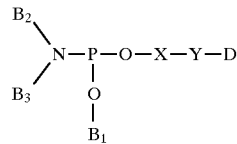

where X is a spacer arm; D is an asymmetric benzoxanthene dye of Formula I or a protected derivative thereof, Y is a linkage formed with a linking group on the dye; B, is a phosphite ester protecting group, and $B_2$, and $B_3$ taken separately are lower alkyl, lower alkene, lower aryl having between 1 and 8 carbon atoms, aralkyl, or cycloalkyl containing up to 10 carbon atoms. Non-nucleotidic phosphorarnidites as shown in Formula IV are particularly well suited for labeling the 5'-end of a chemically-synthesized polynucleotide through the sugar-portion of the nucleotide.

Spacer X and linkage Y may take a variety of forms, however, the structure X—Y must be such that (i) it is stable to DNA synthesis conditions, (ii) does not interfere with oligonucleotide-target hybridization, and (iii) does not quench the fluorescence of the dye to which it is attached, e.g., U.S. Pat. Nos. 5,231,191, 5,258,538, and 4,757,141, 5,212,304, all patents hereby incorporated by reference.

Preferably X is linear or cyclic lower alkyl linear or cyclic substituted lower alkyl polyethlene oxide, lower aryl having between 1 and 8 carbon atoms, peptide, or polyether. Preferably the linkage Y is amido, sulfonanido, urea, urethane, or thourea. In one particularly preferred embodiment, the linkage Y is amido and the spacer X is linear alkyl having the structure below in Formula IV.1

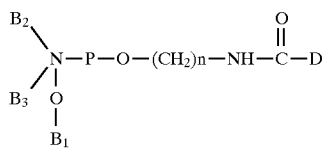

where n is from 2 to 30, preferably from 2 to 10, and more preferably from 2 to 6. In a second particularly preferred embodiment, the linkage Y is amido and the spacer X is linear polyethylene oxide having the structure shown below in Formula IV.2

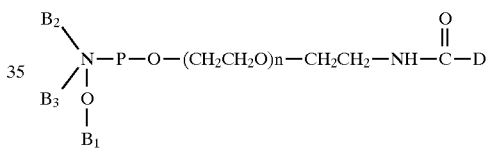

where n is from 2 to 30, preferably from 2 to 10, and more preferably from 2 to 6.

Preferably, $B_2$ and $B_3$ taken together form an alkyl chain containing up to 5 carbon atoms in the principle chain and a total of up to 10 carbon atoms with both terminal valence bonds of said chains being attached to the nitrogen atom. Alternatively, $B_2$ and $B_3$ taken together with the nitrogen atom form a saturated nitrogen heterocycle which contains one or more heteroatoms selected from the group consisting of nitrogen, oxygen, and sulfur.

Case No. 4299 Preferably, $B_2$ and $B_3$ taken separately are isopropyl, t-butyl, isobutyl, or sec-butyl, and $B_2$ and $B_3$ taken together is morphollino.

$B_1$ is a phosphite ester protecting group which prevents unwanted extension of the polynucleotide to which the phosphoramidite is attached. $B_1$ is stable to polynucleotide synthesis conditions yet is able to be removed from the polynucleotide product with a reagent that does not adversely affect the integrity of the polynucleotide or the dye. Preferably, $B_1$ is methyl, β-cyanoethyl, or 4-nitrophenylethyl. $B_2$ and $B_3$ taken separately are isopropyl, t-butyl, isobutyl, or sec-butyl, and $B_2$ and $B_3$ taken together is morphollino.

The linkage linking Y and D is attached to D at one of positions $R_1$–$R_9$. Preferably, the linkage is not attached at $R_1$–$R_3$. When the dyes of the invention are synthesized from trimelletic anhydride, $R_9$ is preferably substituted phenyl and the linkage is attached to the dye at one of the $X_3$ or $X_4$ positions of the substituted phenyl.

Such phosphoramidite compounds may be synthesized by known methods. Generally, the synthesis proceeds as follows. Phenolic hydroxyls of the dye are protected with dye-protecting groups that can be removed with a DNA synthesis deprotection agent, e.g., ammonia, ethanolamine, methylamine/ammonium hydroxide mxtures, and mixtires of t-butylamine/water/methanol (1:2:1), e.g., see U.S. Pat. no. 5,231,191, hereby incorporated by reference in its entirety. Dyes so protected are referred to herein as "protected derivatives" of the dye. Preferred protecting groups include esters of benzoic acid or pivalic acid. The linking group of the protected dye, e.g., carboxylic acid, is then activated, e.g., with carbodiimide, and reacted with an alcohol linker derivative, e.g., an amino alcohol, e.g., ethanolamine, hexanol amine, or the like, in N,N-dimethylformamide (DF), or another like aprotic solvent to yield a protected dye with a free alcohol functionality, e.g., alcohol-amide derivative. The free alcohol is then reacted with a phosphitylating agent using standard procedures, e.g., di-(N,N-diisopropylamino)methoxyphosphine in acetonitrile containing catalytic amounts of tetrazole diisopropylamine, to yield the phosphoramidite, e.g., U.S. Pat. No. 5,231,191.

2. Nucleotidic Phosphoramidite Reagents: Generally, in a second aspect, the phosphorarnidite reagents of the invention have the structure of Formula V immediately below,

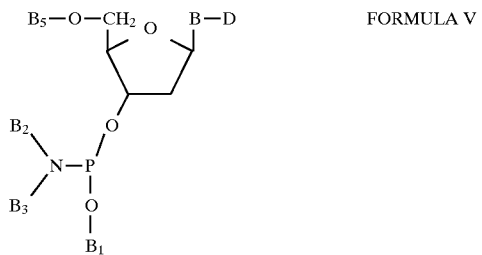

FORMULA V where $B_1$–$B_3$ are as described above, $B_5$ is hydrogen or a hydroxyl protecting group, B is a nucleotide base, and D is an asymmetric benzoxanthene dye of Formula I, or a protected derivative thereof. Nucleotide phosphoramidites such as shown in Formula V are particularly well suited for the internal labeling of chemically-synthesized polynucleotides.

When B is purine or 7-deazapurine, the sugar moiety is attached at the $N^9$-position of the purine or deazapurine. Alternatively, when B is pyrimidine, the sugar moiety is attached at the $N^1$-position of the pyrimidine. B and D are linked through a linkage formed by the reaction of a linking group and its complementary functionality, such linkages between dyes and nucleotide bases have been described in detail above. If B is a purine, the linkage is attached to the 8-position of the purine, while if B is 7-deazapurine, the linkage is attached to the 7-position of the 7-deazapurine. If B is pyrimidine, the linkage is attached to the 5-position of the pyrimidine.

$B_5$ refers generally to hydrogen or an acid-cleavable hydroxyl protecting group. Preferably, $B_5$ is the triphenylmethyl radical and its electron-donating-substituted derivatives, where, as used herein, the term "electron-donating" denotes the tendency of a substituent to release valence electrons to neighboring atoms in the molecule of which it is a part, i.e., it is electropositive with respect to neighboring atoms. Preferably, electron-donating substituents include amino, lower alkyl, lower aryl having between 1 and 8 carbon atoms, lower alkoxy, and the like. More preferably, the electron-donating substituents are methoxy. Exemplary trityls include 4,4'-dimethoxytrityl, i.e. bis(p-anisyl)phenylmethyl, monomethoxytrityl, α-naphthyldiphenylmethyl, tri(p-methoxyphenyl)methyl, and the like. Attachment and cleavage conditions for these and other trityls can be found in Greene and Wuts, *Protective Groups in Organic Synthesis,* 2nd Edition (John Wiley, New York, 1991).

Generally, the nucleotide phosphoramidites of the invention may be synthesized as follows. A nucleoside bearing a hydroxyl protecting group on the 5'- hydroxyl and a protected complementary functionality on the base is selectively deprotected to expose only the complementary functionality. Next, a protected dye (as described above) is activated by converting a linking group into its reactive form. The activated linking group of the dye is then reacted with the complementary functionality of the nucleoside to form the dye labeled nucleoside that bears protecting groups on the 5'-hydroxyl (and on the 2'-hydroxyl for the case of RNA) and on the phenolic groups of the dye. The dye labeled nucleoside is then reacted with a phosphitylating agent as described above to produce the nucleotide phosphoramidite.

In a preferred method where the complementary functionality is amine and the linking group is carboxyl, the synthesis proceeds as follows. A protected nucleoside bearing a hydroxyl protecting group on the 5'- hydroxl, e.g., a trityl group, and a protected amino-nitrogen complementary functionality on the base is selectively deprotected to expose the amine, such selective deprotection serving to deprotect only the amine functionality without deprotecting the protected 5'-hydroxyl moiety. A protected dye (as described above) is activated by converting a carboxy linking group into its NHS ester with dicyclohexyl carbodiimide and N-hydroxysuceimmide. The NHS ester is reacted with the amino group of the nucleoside to form the dye labeled nucleoside that bears protecting groups on the 5'-hydroxyl (and on the 2'-hydroxyl for the case of RNA) and on the phenolic groups of the dye. The dye labeled nucleoside is then reacted with a phosphitylating agent as described above.

C. Polynucleotide Reagents

Yet another preferred class of reagents of the present invention comprise polynucleotides labeled with the asymmetric benzoxanthene dyes of the invention. Such labeled polynucleotides are useful in a number of important contexts including as DNA sequencing primers, PCR primers, oligonucleotide hybridization probes, and the like.

As used herein, the terms "polynucleotide" or "oligonucleotide" refer to linear polymers of natural or modified nucleoside monomers, including double and single stranded deoxyribonucleosides, ribonucleosides, α-anomeric forms thereof and the like. Usually the nucleoside monomers are linked by phosphodiester linkages, where as used herein, the term "phosphodiester linkage" refers to phosphodiester bonds or analogs thereof including phosphorothioate, phosphorodithioate, phosphoroselenoate, phosphorodiselenoate, phosphoroanilothioate, phosphoranilidate, phosphoramidate, and the like, including associated counterions, e.g., H, $NH_4$, Na, and the like if such counterions are present. The * polynucleotides range in size form a few monomeric units, e.g. 8–40, to several thousands of monomeric units. Whenever a polynucleotide is represented by a sequence of letters, such as "ATGCCTG," it will be understood that the nucleotides are in 5'–>3' order from left to right and that "A" denotes deoxyadenosine, "C" denotes deoxycytidine, "G" denotes deoxyguanosine, and "T" denotes thymidine, unless otherwise noted.

The labeled polynucleotides of the invention include a nucleotide having the formula:

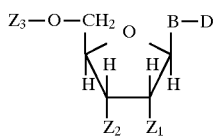

FORMULA VI where B is a 7-deazapurine, purine, or pyriridine nucleotide base. $Z_1$ is H or OH. $Z_2$ is H, OH, $HPO_4$, or Nuc, wherein Nuc refers to a nucleoside or polynucleotide. The nucleoside of Formula VI and Nuc are linked by a phosphodiester linkage, the linkage being attached to the 5'-position of Nuc. $Z_3$ is H, HPO3, or Nuc, wherein Nuc and the nucleoside are linked by a phosphodiester linkage attached to the 3'-position of Nuc. D is a dye compound of Formula I. Base B is attached to the sugar moiety and to the dye compound as described above for the nucleotide phosphoramidite reagent of the invention. As defined, the labeled nucleotide of Formula VI can be the 5'-terminal nucleotide, the 3'-terminal nucleotide, or any internal nucleotide of the polynucleotide.

In one preferred embodiment, the labeled polynucleotides of the present invention include multiple dyes located such that fluorescence energy transfer takes place between a donor dye and an acceptor dye. Such multi-dye polynucleotides find application as spectrally-tunable sequencing primers, e.g., Ju et al., *Proc. Natl. Acad. Sci. USA* 92: 4347–4351 (1995), and as hybridization probes, e.g., Lee et al. *Nucleic Acids Research,* 21: 3761–3766 (1993).

Labeled polynucleotides may be synthesized either enzymatically, e.g., using a DNA polymerase or ligase, e.g., Stryer, *Biochemistry,* Chapter 24, W. H. Freeman and Company (1981), or by chemical synthesis, e.g., by the phosphoramidite method, the phosphite-triester method, and the like, e.g., Gait, *Oligonucleotide Synthesis,* IRL Press (1990). Labels may be introduced during enzymatic synthesis utilizing labeled nucleotide triphosphate monomers as described above, or introduced during chemical synthesis using labeled non-nucleotide or nucleotide phosphoramidites as described above, or may be introduced subsequent to synthesis.

Generally, if the labeled polynucleotide is made using enzymatic synthesis, the following procedure may be used. A template DNA is denatured and an oligonucleotide primer is annealed to the template DNA A mixture of deoxynucleotide triphosphates is added to the reaction including dGTP, dATP, dCTP, and dTTP where at least a fraction of one of the Case No. 4299 deoxynucleotides is labeled with a dye compound of the invention as described above. Next, a polymerase enzyme is added under conditions where the polymerase enzyme is active. A labeled polynucleotide is formed by the incorporation of the labeled deoxynucleotides during polymerase strand synthesis. In an alternative enzymatic synthesis method, two primers are used instead of one, one primer complementary to the + strand and the other complementary to the − strand of the target, the polymerase is a thermostable polymerase, and the reaction temperature is cycled between a denaturation temperature and an extension temperature, thereby exponentially synthesizing a labeled complement to the target sequence by PCR, e.g., *PCR Protocols,* Innis et al. eds., Academic Press (1990).

Labeled polynucleotides may be chemically synthesized using the phosphoramidite method. Detailed descriptions of the chemistry used to form polynucleotides by the phosphoramidite method are provided elsewhere, e.g., Caruthers et al., U.S. Pat. No. 4,458,066; Caruthers et al., U.S. Pat. No. 4,415,732; Caruthers et al., *Genetic Engineering,* 4: 1–17 (1982); *Users Manual Model* 392 *and* 394 *Polynucleotide Synthesizers,* pages 6–1 through 6–22, Applied Biosystems, Part No. 901237 (1991). Accordingly, each of these references are hereby incorporated by reference in their entirety.

The phosphoramidite method of polynucleotide synthesis is the preferred method because of its efficient and rapid coupling and the stability of the starting materials. The synthesis is performed with the growing polynucleotide chain attached to a solid support, so that excess reagents, which are in the liquid phase, can be easily removed by filtration, thereby eliminating the need for purification steps between cycles.

The following briefly describes the steps of a typical polynucleotide synthesis cycle using the phosphoramidite method. First, a solid support including a protected nucleotide monomer is treated with acid, e.g., trichloroacetic acid, to remove a 5'-hydroxyl protecting group, freeing the hydroxyl for a subsequent coupling reaction. An activated intermediate is then formed by simultaneously adding a protected phosphoramidite nucleoside monomer and a weak acid, e.g., tetrazole, to the reaction. The weak acid protonates the nitrogen of the phosphoramidite forming a reactive intermediate. Nucleoside addition is complete within 30 s. Next, a capping step is performed which terminates any polynucleotide chains that did not undergo nucleoside addition. Capping is preferably done with acetic anhydride and 1-methylimidazole. The internucleotide linkage is then converted from the phosphite to the more stable phosphotriester by oxidation using iodine as the preferred oxidizing agent and water as the oxygen donor. After oxidation, the hydroxyl protecting group is removed with a protic acid, e.g., trichloroacetic acid or dichloroacetic acid, and the cycle is repeated until chain elongation is complete. After synthesis, the polynucleotide chain is cleaved from the support using a base, e.g., ammonium hydroxide or t-butyl amine. The cleavage reaction also removes any phosphate protecting groups, e.g., cyanoethyl. Finally, the protecting groups on the exocyclic amines of the bases and the hydroxyl protecting groups on the dyes are removed by treating the polynucleotide solution in base at an elevated temperature, e.g., 55 ° C.

Any of the phosphoramidite nucleoside monomers may be dye-labeled phosphoramidites as described above. If the 5'-terminal position of the nucleotide is labeled, a labeled non-nucleotidic phosphoramidite of the invention may be used during the final condensation step. If an internal position of the oligonucleotide is to be labeled, a labeled nucleotidic phosphoramidite of the invention may be used during any of the condensation steps.

Subsequent to synthesis, the polynucleotide may be labeled at a number of positions including the 5'-terminus, e.g., *Oligonucleotides and Analogs,* Eckstein ed., Chapter 8, IRL Press (1991) and Orgel et al., *Nucleic Acids Research* 11(18): 6513 (1983); U.S. Pat. No. 5,118,800, hereby incorporated by reference; the phosphodiester backbone, e.g., ibid., Chapter 9; or at the 3'-terminus, e.g., Nelson, *Nucleic Acids Research* 20(23): 6253–6259, and U.S. Pat. Nos. 5,401,837 and 5,141,813, both patents hereby incorporated by reference. For a review of oligonucleotide labeling procedures see R. Haugland in *Excited States of Biopolymers,* Steiner ed., Plenum Press, NY (1983).

In one preferred post-synthesis chemical labeling method an oligonuleotide is labeled as follows. A dye including a carboxy linking group is converted to the n-hydroxysuccinimide ester by reacting with approximately 1 equivalent of 1,3-dicyclohexylcarbodiimide and approximately 3 equivalents of n-hydroxysuccinnnlde in dry ethyl acetate for 3 hours at room temperature. The reaction mixture is washed with 5% HCI, dried over magnesium sulfate, filtered, and concentrated to a solid which is resuspended in DMSO. The DMSO dye stock is then added in excess (10–20 x) to an aminohexyl derivatized oligonucleotide in 0.25 M bicarbonatejcarbonate buffer at pH 9.4 and allowed to react for 6 hours, e.g., U.S. Pat. No. 4,757,141. The dye labeled oligonucleotide is separated from unreacted dye by passage through a size-exclusion chromatography column eluting with buffer, e.g., 0.1 molar triethylainie acetate (TEAA). The fraction containing the crude labeled oligonucleotide is further purified by reverse phase HPLC employing gradient elution.

IV. Methods Utilizing the Compounds and Reagents of the Invention

The dyes and reagents of the present invention are well suited to any method utilizing fluorescent detection, particularly methods requiring the simultaneous detection of multiple spatially-overlapping analytes. Dyes and reagents of the invention are particularly well suited for identifying classes of polynucleotides that have been subjected to a biochemical separation procedure, such as electrophoresis, where a series of bands or spots of target substances having similar physiochemical properties, e.g. size, conformation, charge, hydrophobicity, or the like, are present in a linear or planar arrangement. As used herein, the term "bands" includes any spatial grouping or aggregation of analytes on the basis of similar or identical physiochemical properties. Usually bands arise in the separation of dye-polynucleotide conjugates by electrophoresis.

Classes of polynucleotides can arise in a variety of contexts. In a preferred category of methods referred to herein as "fragment analysis" or "genetic analysis" methods, labeled polynucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a particularly preferred embodiment, multiple classes of polynucleotides are separated simultaneously and the different classes are distinguished by spectrally resolvable labels.

One such fragment analysis method known as amplified fragment length polymorphisim detection (AmpFLP) is based on amplified fragment length polymorphisms, i.e., restriction fragment length polymorphisms that are amplified by PCR. These amplified fragments of varying size serve as linked markers for following mutant genes through families. The closer the amplified fragment is to the mutant gene on the chromosome, the higher the linkage correlation. Because genes for many genetic disorders have not been identified, these linkage markers serve to help evaluate disease risk or paternity. In the AmpFLPs technique, the polynucleotides may be labeled by using a labeled polynucleotide PCR primer, or by utilizing labeled nucleotide triphosphates in the PCR.

In another such fragment analysis method known as nick translation, a reaction is used to replace unlabeled nucleoside triphosphates in a double-stranded DNA molecule with labeled ones. Free 3'-hydroxyl groups are created within the unlabeled DNA by "nicks" caused by deoxyribonuclease I (DNAase I) treatment. DNA polymerase I then catalyzes the addition of a labeled nucleotide to the 3'-hydroxyl terminus of the nick. At the same time, the 5' to 3'-exonuclease activity of this enzyme eliminates the nucleotide unit from the 5'-phosphoryl terminus of the nick. A new nucleotide with a free 3'-OH group is incorporated at the position of the original excised nucleotide, and the nick is shifted along by one nucleotide unit in the 3' direction. This 3' shift will result in the sequential addition of new labeled nucleotides to the DNA with the removal of existing unlabeled nucleotides. The nick-translated polynucleotide is then analyzed using a separation process, e.g., electrophoresis.

Another exemplary fragment analysis method is based on variable number of tandem repeats, or VNTRs. VNTRs are regions of double-stranded DNA that contain adjacent multiple copies of a particular sequence, with the number of repeating units being variable. Examples of VNTR loci are pYNZ22, pMCT118, and Apo B. A subset of VNTR methods are those methods based on the detection of microsatellite repeats, or short tandem repeats (STRs), i.e., tandem repeats of DNA characterized by a short (2–4 bases) repeated sequence. One of the most abundant interspersed repetitive DNA families in humans is the (dC-dA)n—(dG-dT)n dinucleotide repeat family (also called the (CA)n dinucleotide repeat family). There are thought to be as many as 50,000 to 100,000 (CA)n repeat regions in the human genome, typically with 15–30 repeats per block. Many of these repeat regions are polymorphic in length and can therefore serve as useful genetic markers. Preferably, in VNTR or STR methods, label is introduced into the polynucleotide fragments by using a dye-labeled PCR primer.

In a particularly preferred fragment analysis method, classes identified in accordance with the invention are defined in terms of terminal nucleotides so that a correspondence is established between the four possible terminal bases and the members of a set of spectrally resolvable dyes. Such sets are readily assembled from the dyes of the invention by measuring emission and absorption bandwidths with commercially available spectrophotometers. More preferably, the classes arise in the context of the chemical or chain termination methods of DNA sequencing, and most preferably the classes arise in the context of the chain termination method, i.e., dideoxy DNA sequencing, or Sanger sequencing. This method involves the synthesis of a DNA strand by a DNA polymerase in vitro using a single-stranded or double-stranded DNA template whose sequence is to be determined. Synthesis is initiated at only the one site where an oligonucleotide primer anneals to the template. The synthesis reaction is terminated by incorporation of a nucleotide analog that will not support continued DNA elongation. The chain-terminating nucleotide analogs are the 2',3'-dideoxynucleoside 5'-triphosphates (ddNTPs) which lack the 3'-OH group necessary for 3' to 5' DNA chain elongation. When proper proportions of dNTPs (2'-deoxynucleoside 5'-triphosphates) and one of the four ddNTPs are used, enzyme-catalyzed polymerization will be terminated in a fraction of the population of chains at each site where the ddNTP can be incorporated. If labeled primers or labeled ddNTPs are used for each reaction, the sequence information can be detected by fluorescence after separation by high-resolution electrophoresis. In the chain termination method, dyes of the invention can be attached to either sequencing primers or dideoxynucleotides. Dyes can be linked to a complementary functionality on the 5' end of the primer, e.g. following the teaching in Fung et al, U.S. Pat. No. 4,757,141 which is incorporated herein by reference; on the base of a primer; or on the base of a dideoxynucleotide, e.g. via the alkynylamino linking groups disclosed by Hobbs et al, European patent application number 87305844.0 which is discussed above and incorporated herein by reference.

In each of the above fragment analysis methods labeled polynucleotides are preferably separated by electrophoretic procedures, e.g. Gould and Matthews, cited above; Rickwood and Hames, Eds., *Gel Electrophoresis of Nucleic Acids: A Practical Approach,* (IRL Press Limited, London, 1981); or Osterman, *Methods of Protein and Nucleic Acid Research,* Vol. 1 Springer-Verlag, Berlin, 1984). Preferably the type of electrophoretic matrix is crosslinked or uncrosslinked polyacrylamide having a concentration (weight to volume) of between about 2–20 weight percent. More preferably, the polyacrylamnide concentration is between about 4–8 percent. Preferably in the context of DNA sequencing in particular, the electrophoresis matrix includes a strand separating, or denaturing, agent, e.g., urea, formarnide, and the like. Detailed procedures for constructing such matrices are given by Maniatis et al., "Fractionation of Low Molecular Weight DNA and RNA in Polyacrylamide Gels Containing 98% Formamide or 7 M Urea," in *Methods in Enzymology,* 65: 299–b 305 (1980); Maniatis et al., "Chain Length Determination of Small Double- and Single-Stranded DNA Molecules by Polyacrylamide Gel Electrophoresis," *Biochemistry,* 14: 3787–3794 (1975); Maniatis et al., *Molecular Cloning: A Laboratory Manual* (Cold Spring Harbor Laboratory, New York, 1982), pgs. 179–185; and *ABI PRISM™377 DNA Sequencer User's Manual, Rev. A,* Jan. 1995, Chapter 2 (p/n 903433, The Perkin-Elmer Corporation, Foster City, Calif.). Accordingly these references are incorporated by reference. The optimal polymer concentration, pH, temperature, concentration of denaturing agent, etc. employed in a particular separation depends on many factors, including the size range of the nucleic acids to be separated, their base compositions, whether they are single stranded or double stranded, and the nature of the classes for which information is sought by electrophoresis. Accordingly application of the invention may require standard preliminary testing to optimize conditions for particular separations. By way of example, oligonucleotides having sizes in the range of between about 20–300 bases have been separated and detected in accordance with the invention in the following matrix: 6 percent polyacrylamide made from 19 parts to 1 part acrylamide to bis-acrylamide, formed in a Tris-borate EDTA buffer at pH 8.3.

Subsequent to electrophoretic separation, the dye-polynucleotide conjugates are detected by measuring the fluorescence emission from the dye labeled polynucleotides. To perform such detection, the labeled polynucleotides are illuminated by standard means, e.g. high intensity mercury vapor lamps, lasers, or the like. Preferably the illumination means is a laser having an illumination beam at a wavelength between 488 and 550 nm. More preferably, the dye-polynucleotides are illuminated by laser light generated by an argon ion laser, particularly the 488 and 514 nm emission lines of an argon ion laser, or an the 532 emission line of a neodymium solid-state YAG laser. Several argon ion lasers are available commercially which lase simultaneously at these lines, e.g. Cyonics, Ltd. (Sunnyvale, Calif.) Model 2001, or the like. The fluorescence is then detected by a light-sensitive detector, e.g., a photomultiplier tube, a charged coupled device, or the like.

IV. Examples

The invention will be further clarified by a consideration of the following examples, which are intended to be purely exemplary of the invention and not to in any way limit its scope.

Unless otherwise indicated, all chemicals were obtained from Aldrich Chemical Company (Milwaukee, Wis.) and used as purchased. 3-Fluororesorcinol (11a) was synthesized from 2,4iethoxyanihne according to the literature procedure (Perkin, *J Chem Soc.* 110: 1658–1666 (1980)). 2-Chloro-4-methoxyresorcinol (11c) was synthesized from 3-hydroxy4-methoxy-benzaldehyde according to U.S. Pat. No. 4,318,846. 3,6-Dichlorotrimellitic acid was synthesized according to U.S. Pat. No. 4,318,846, and converted to the anhydride 10a by refluxing in neat acetic anhydride for 4 hours and precipitation of the cooled mixture with diethyl ether. Ethyl hydrogen fluoromalonate was synthesized from diethyl fluoromalonate according to the literature (*Org. Syn. Coll.* 4: 417419 (1963)). Ethyl tributylphosponium-fluoroacetate (19) was synthesized according to the literature (*Tet. Lett.* 30: 6113 (1980)). 2-Fluoro-1,3-dihydroxynapthalene (9a) was synthesized as described in the present disclosure. Dry dichloromethane ($CH_2Cl_2$) was distilled from calcium hydride and tetrahydrofuran (THF) from lithium aluminum hydride (LAH) prior to use. Absolute ethanol was used as purchased or dried by distillation from sodium and stored over activated molecular sieves. Dry ethyl acetate (EtOAc) was distilled from $P_2O_5$ after pre-drying with $MgSO_4$. Dry dimethylformamide (DMF) was distilled after pre-drying with magnesium sulfate and stored over activated molecular sieves. All reactions were run under anhydrous conditions under dry argon. Reactions were monitored by thin layer chromatography (TLC) (Silica gel 60, $A_{254}$). Flash chromatography was performed on silica gel 60 (200–400 mesh, Baxter). Final purification of the asymmetric benzoxanthene dyes to give the pure isomers, designated "1" and "2", employed preparative TLC on silica gel 60 PTLC plates AM Science) eluting with $CH_2Cl_2$: MEOH: AcOH (7:3:0.1). Pure dye isomers were identified by giving a single spot on TLC employing $CH_2Cl_2$: MeOH: AcOH (7:3:0.1) and visualizing with short and long-wavelength UV irradiation Isomer 2 rnns slower on both normal and reverse-phase media. Intermediate products were identified by $^1$HNMR spectra on a Varian 300 MHz NMR. Absorption spectra of the purified dyes were recorded on a Hewlett Packard 8451A diode array spectrophotometer, and fluorescence emission spectra were recorded on a Perkin Elmer LS 50-B luminescence spectrophotometer. HPLC purification of dye labeled oligonucleotides was performed on a Perkin-Elmer 200 series pump, connected to a PE LC 240 fluorescence detector, and a PE LC 295 UV/VIS detector, connected to a 2 channel PE 1022 integrator. Buffers employed for dye labeled oligonucleotide purification and identification include tris(hydroxymethyl) aminomethane/borate/EDTA (TBE), tris(hydroxymethyl) amninomethane/EDTA(TE), triethylammonium acetate (TEAA). Buffers are stored as 10×solutions at 0° C. and diluted fresh before use. HPLC purification employed a reverse-phase RP-18 column.

EXAMPLE 1

Synthesis of Asymmetric Benzoxanthenes

Compounds 1–7 in FIGS. 2A and 2B were synthesized by reacting a 1,3 dihydroxynapthalene derivative, such as 1,3-dihydroxynapthalene 9b or 2-fluoro-1,3-dihydroxynapthalene 9a (0.2 mole), with 1.1 equivalent of the phthailic anhydride derivative 3,6-dichlorotrimelletic acid anhydride 10a, and one equivalent of a resorcinol derivative 11 (0.2 mole), 11a, 11b, 11c, or 11d depending on the final product desired, and heated for 16 hours in neat $MeSO_3H$ (3 ml) at 110° C. under Argon. The crude dye (a mixture of regioisomers in reactions employing 10a) was precipitated by addition to an ice/water mixture and isolated by filtration. The crude dye was purified into 2 isomers 1 and 2 by preparative thin layer chromatography eluting with a mixture of $CH_2Cl_2$: MEOH: Acetic Acid (70:30:1).

The inset in FIG. 2B shows that $R_2$ and/or $R_3$ unsubstituted ($R_2$=$R_3$=H) derivatives of the asynmmetric benzoxanthene dyes, shown for isomer 2 of dye 5, react further with halogenating reagents (NaOCl, NaOH/Br$_2$, NaOH/I$_2$) at 0° C. for 3 hours to produce quantitatively the halogenated derivatives such as 8 (R2=R3=Cl, Br, I, F) after extractive workup with 10% HCI /EtOAc, drying with Na$_2$SO$_4$, filtering, and concentrating in vacuo.

EXAMPLE 2

Synthesis of Dye-labeled Oligonucleotides

Figure 3:
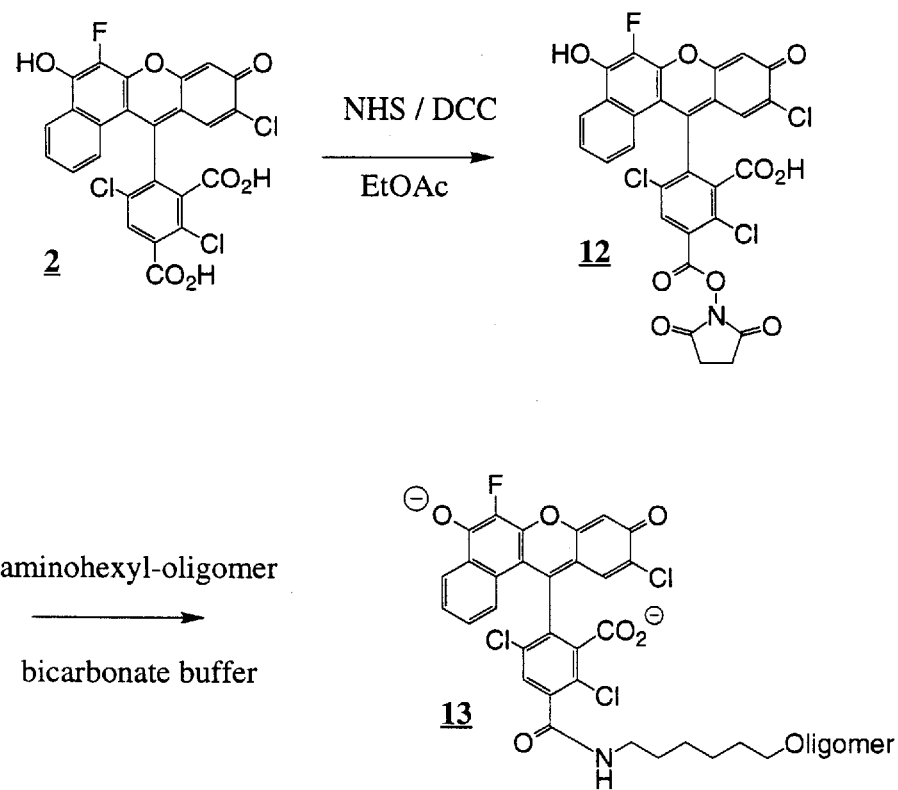
FIG. 3 shows a preferred synthesis of oligonucleotides labeled with the dyes of the invention.

The synthesis of dye labeled oligonucleotides of the invention will be described with reference to FIG. 3. CL-FLAN, dye 2, was converted to the n-hydroxysuccinimide ester 12 by reacting with 1.2 equivalents of 1,3-dicyclohexylcarbodiimide and 3 equivalents of n-hydroxysuccinimide in dry ethyl acetate for 3 hours at room temperature. The reaction mixture was washed with 5% HCI, dried over magnesium sulfate, filtered, and concentrated to a solid which was resuspended in DMSO ( 10 mg dye/50 $\mu$L DMSO). The DMSO dye stock (5–10 $\mu$L) was added in excess (10–20 x) to an aminohexyl derivatized -21M13 oligonucleotide primer (1×10$^{-3}$ M) in 0.25 M bicarbonate/carbonate buffer at pH 9.4 and allowed to react for 6 hours. The aminohexyl derivatized primer was prepared by automated solid-phase DNA synthesis using Amninolink-2 in the last cycle (PE p/n 400808). The dye labeled oligonucleotide was separated from unreacted dye by passage through a Sephadex G-25 column eluting with 0.1 molar triethylamine acetate (TEAA). The fraction containing the crude labeled oligonucleotide was purified by reverse phase HPLC employing gradient elution from 8% AcCN in 0.1 M TEAA to 25% over 25 minutes using an RP-18 chromatography column. The pure dye labeled oligonucleotide 13 was lyophilized to a solid and resuspended in 1×TE buffer pH 8.4. The concentration of the dye labeled oligonucleotide was determined by UV absorption at 260 nm assuming additive extinction coefficient values of 6,650 for T, 7,350 for C, 11,750 for G, and 14,900 for A, and the relative contribution of the dye absorption at 260 nm determined from spectra of the free dye measured in the same buffer.

EXAMPLE 3

Comparison of the Excitation Spectra of TAMRA (22) and Cl-FLAN (2) Labeled Oligonucleotides from Example 2

Figure 4:
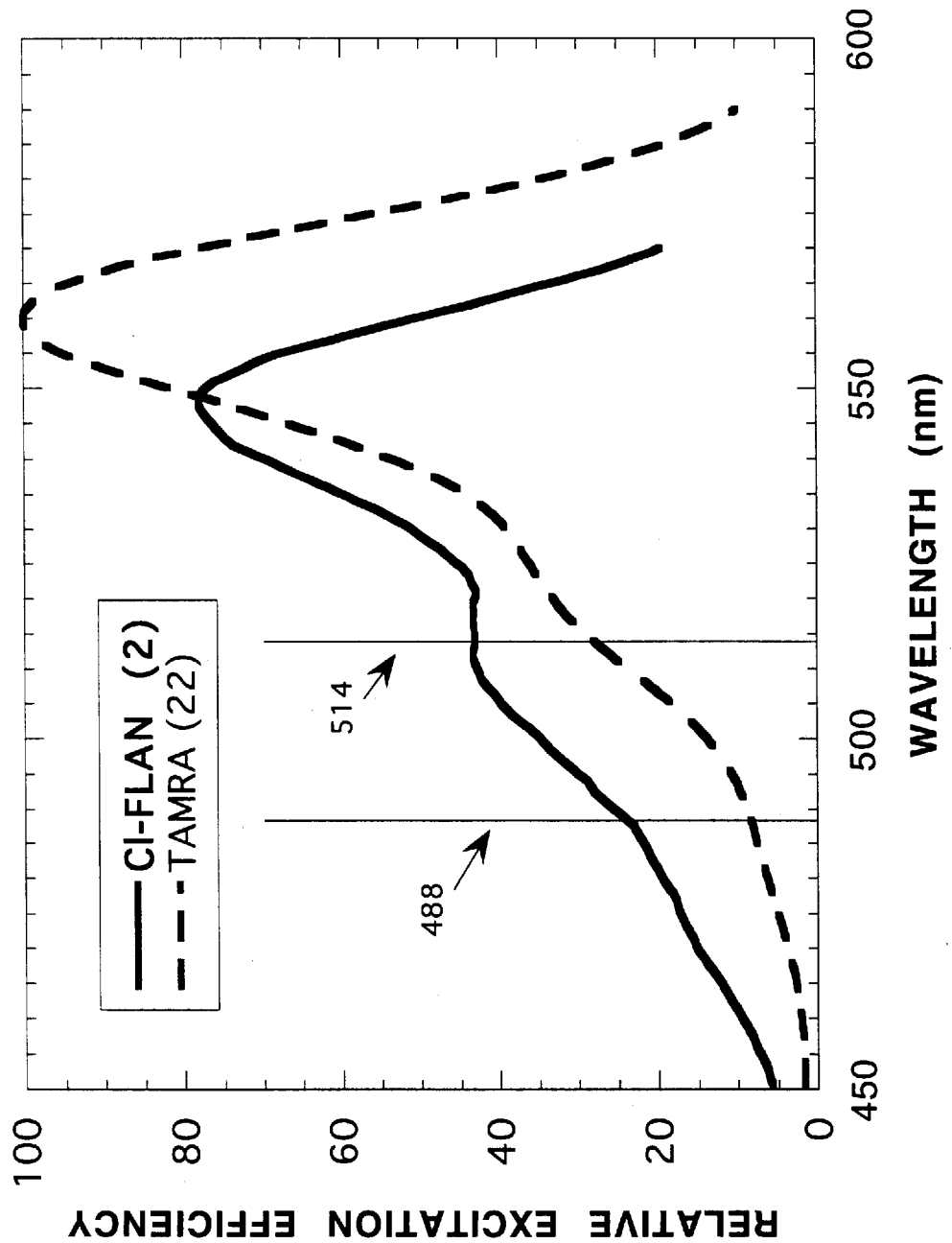
FIG. 4 shows the excitation spectra of TAMRA (22) - and Cl-FLAN (2)-labeled oligonucleotides.

Excitation spectra were recorded for each dye in 1×TBE buffer at pH 8.4. Dyes where present at an equimolar concentration (ca. 1×10$^{-6}$ M). The emission intensity was recorded at $\lambda_{max}$Em for each dye. FIG. 4 shows that for excitation at 488 nm the relative excitation efficiency of Cl-FLAN is approximately 2.5 times that of the TAMRA dye, while for excitation at 514 nm, the relative excitation efficiency of Cl-FLAN is approximately 1.5 times that of the TAMRA dye.

EXAMPLE 4

Comparison of the Quantum Yield of TAMRA (22) and Cl-FLAN (2) Labeled Oligonucleotides from Example 2

Figure 5:
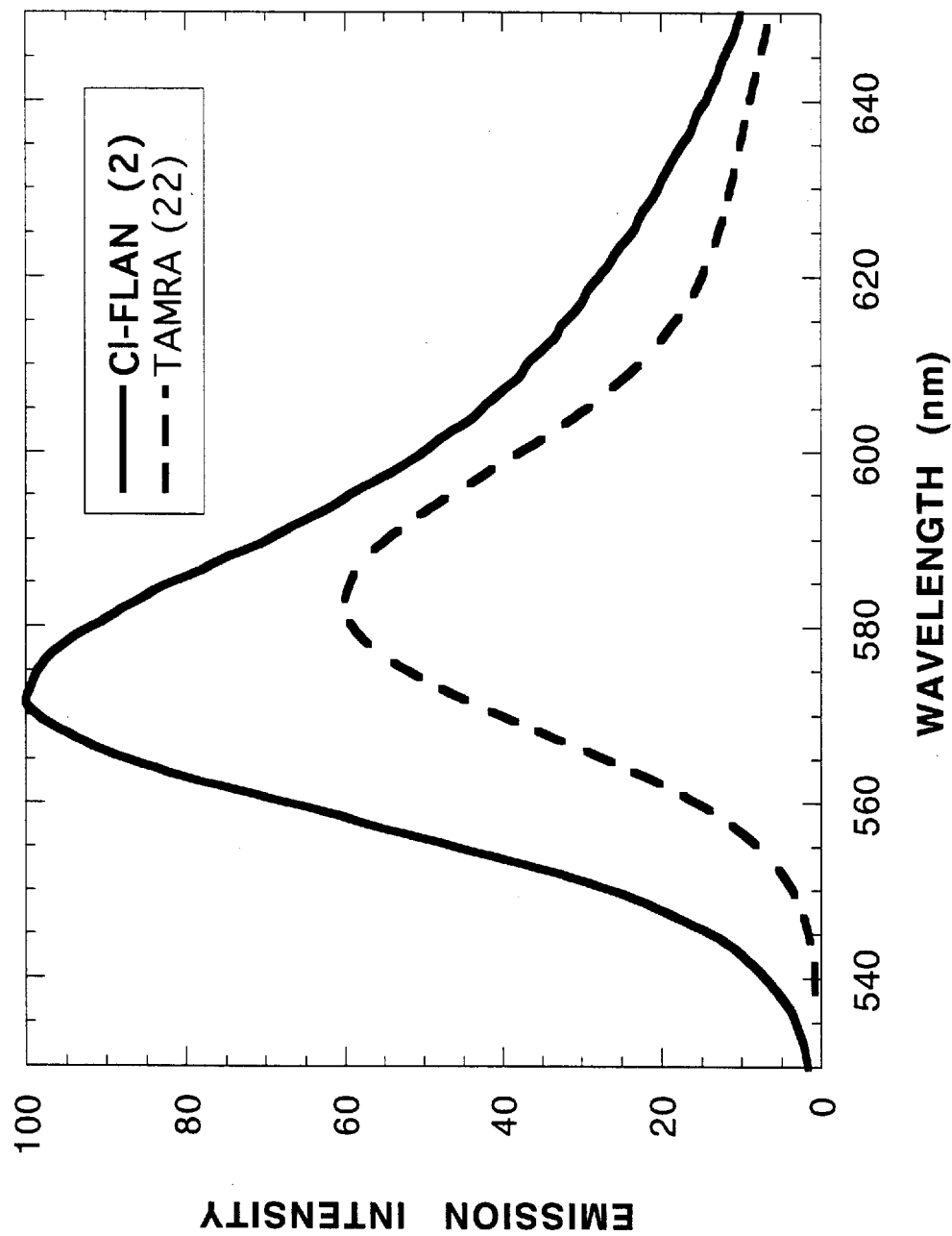
FIG. 5 shows a comparison of the quantum yields of TAMRA (22)- and Cl-FLAN (2)-labeled oligonucleotides.

FIG. 5 shows emission spectra the fluorescense emission intensity of a TAMRA (22) labeled -21M13 oligonucleotide and a Cl-FLAN(2) labeled -21M13 oligonucleotide excited at the absorption maxima of each dye. The oligonucleotides were prepared as in Example 2. The data demonstrate a 60% greater quantum yield for the Cl-FLAN (2) labeled oligonucleotide as compared to the TAMRA (22) labeled oligonucleotide. Spectra were recorded in 1×TE buffer at pH 8.4 at a concentration resulting in an equal $\lambda_{max}$Abs of 0.05 for each labeled oligonucleotide. Emission spectra were recorded for each dye with irradiation at $\lambda_{max}$Abs for each dye.

EXAMPLE 5

Figure 6:
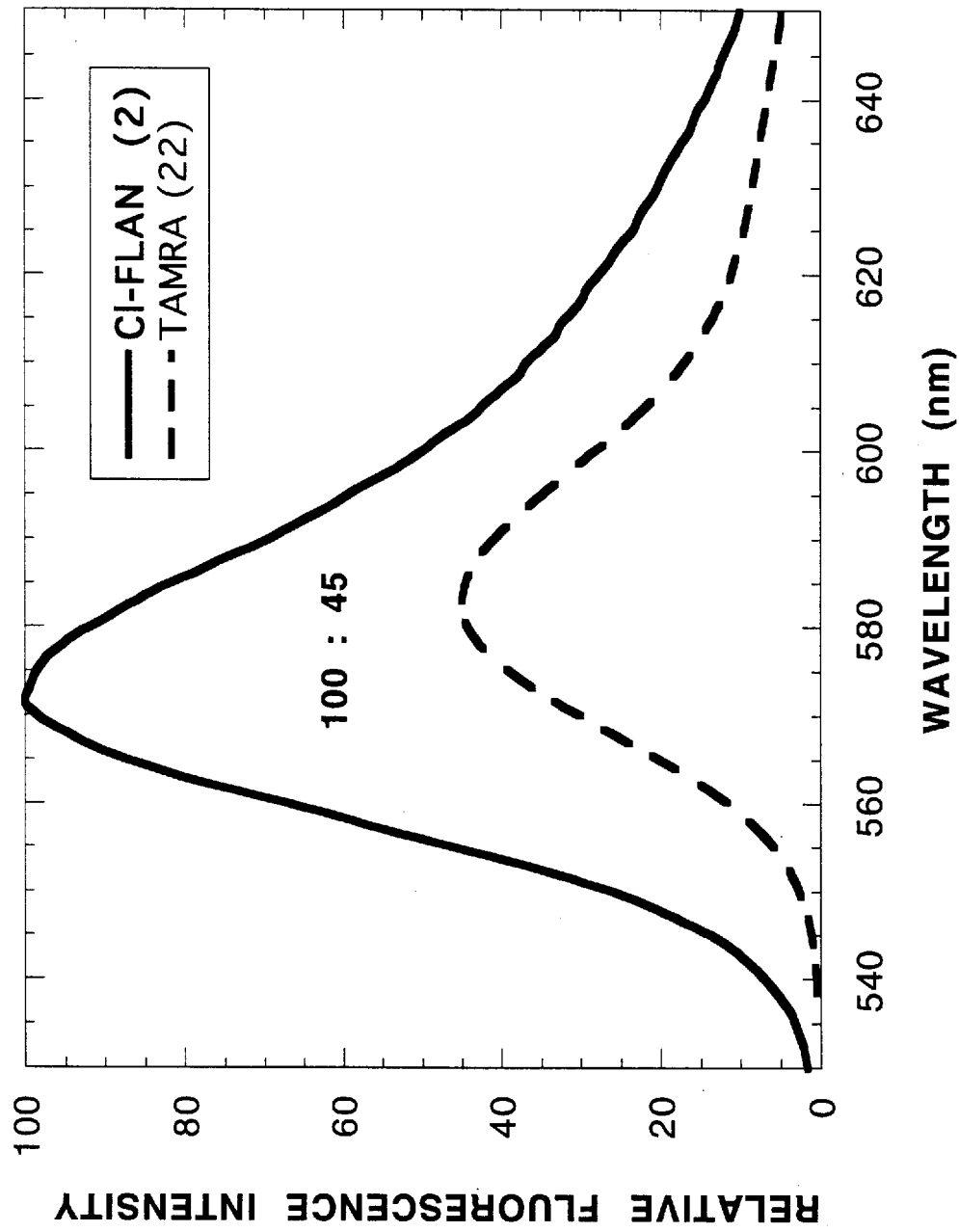
FIG. 6 shows a comparison of the eqimolar emission intensity of TAMRA (22)-and Cl-FLAN (2)-labeled oligonucleotides.

Comparison of the Molar Emission Intensity of Cl-FLAN (2) and TAMPA (22) Labeled Oligonucleotide Emission spectra of equimolar concentrations (ca. 1×10$^{-6}$ M) of a TAMRA (22) labeled oligonucleotide and a Cl-FLAN (2) labeled oligonucleotide dissolved in 1×TE buffer at pH 8.4 were measured by irradiating each oligonucleotide at 488 nm and 514 nm, and adding the spectra to approximate the radiation of a multiline argon laser. FIG. 6 shows that the fluorescence intensity of the Cl-FLAN (2) labeled oligonucleotide is over 2 times greater than that of the TAMRA (22) labeled oligonucleotide.

EXAMPLE 6

Multiplex Dye-labeled Oligonucleotide Set

Figure 7:
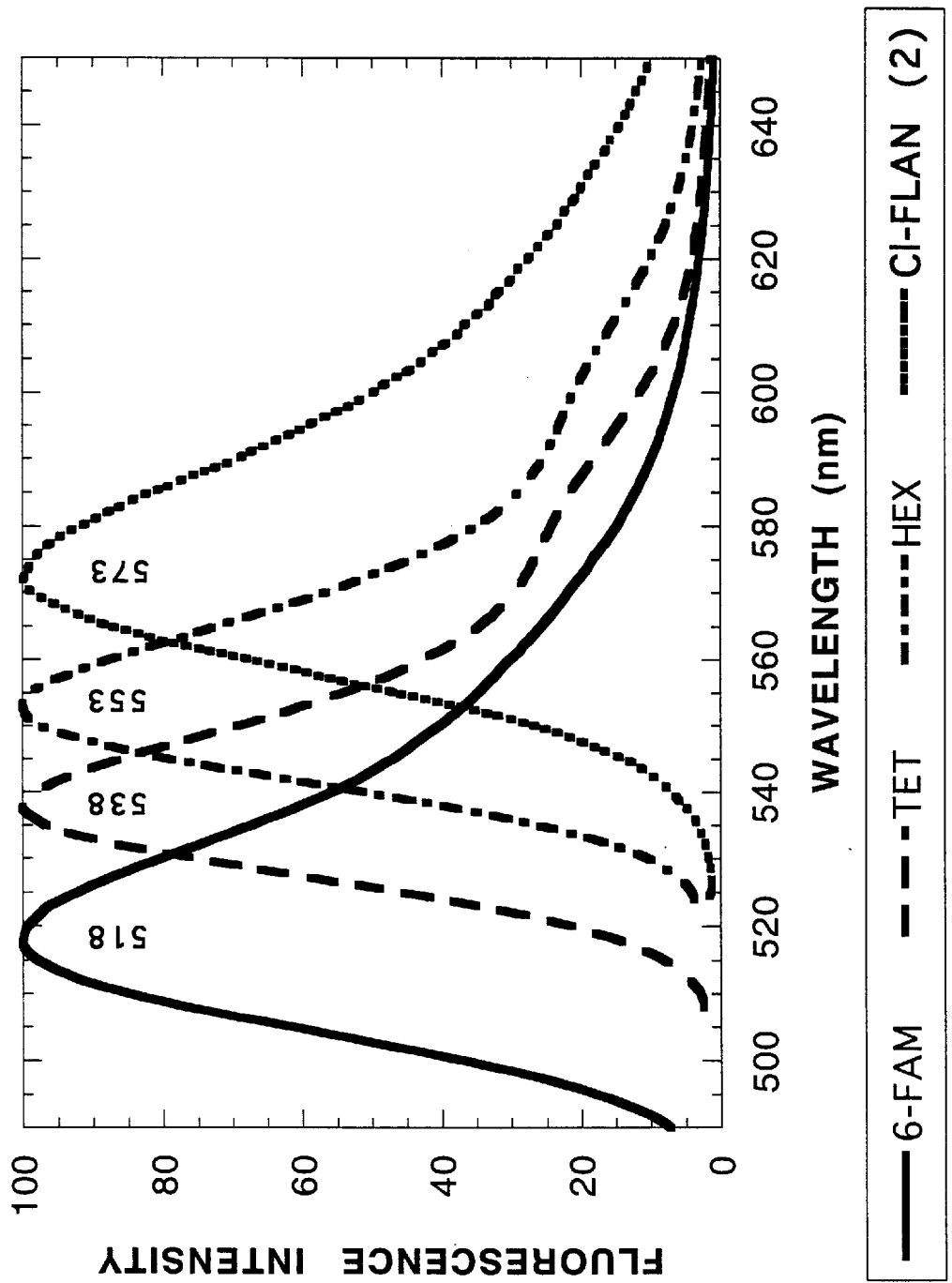
FIG. 7 shows fluorescence emission spectra for members of a 4-plex set of dye-labeled DNA sequencing primers.

Long-wavelength fluorescence emission of a Cl-FLAN (2) labeled oligonucleotide -21M13 sequencing primer was compared with the emission from -21M13 sequencing primers labeled with 6-FAM, TET, and, HEX 23 dyes, where 6-FAM refers to 6-carboxyfluorescein, "TET" refers to 6-carboxy-4,7,2',7'-tetrachlorofluorescein, and "HEX" refers to 6-carboxy-4,7,2',4',5',7',-hexachlorofluorescein. Primers were labeled as described above in Example 2. The excitation wavelength was 490 nm. Emission spectra were run in 1×TE buffer at pH 8.4 and normalized to equal intensity (ca. 1*10$^{-6}$ M). FIG. 7 shows that the 573 nm emission maxima and the narrow width of the emission spectrum of the Cl-FLAN (2) labeled oligonucleotide makes the Cl-FLAN (2) labeled oligonucleotide spectrally resolved from the emission spectra of the other 3 dyes in the set. Such spectral resolution indicates the suitability of a dye set including, FAM, TET, and HEX labeled oligonucleotides with the Cl-FLAN (2) asymmetric benzoxanthene dye.

EXAMPLE 7

Synthesis of a 2-Fluoro-1,3-Dihydroxynapthalene Intermediate

Figure 8:
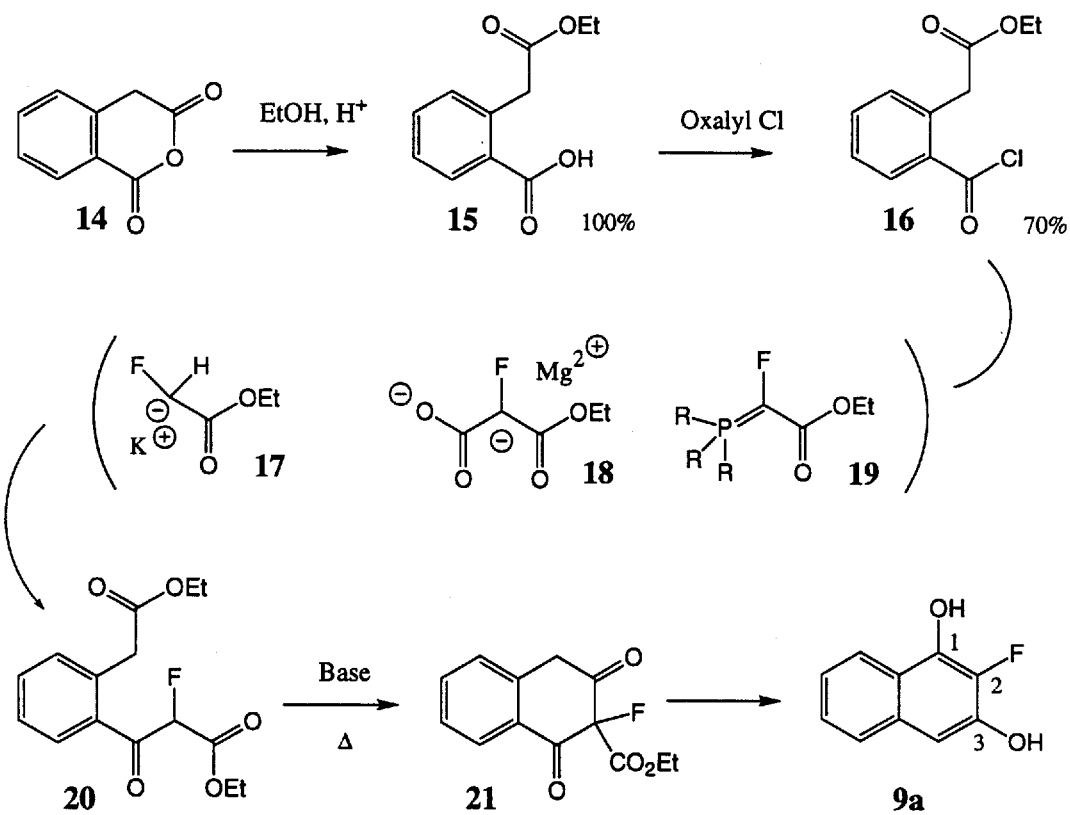
FIG. 8 shows a synthesis of a 2-fluoro-1,3-dihydroxynapthalene intermediate of the invention.

See FIG. 8. Commercially available homopthallic anhydride (14) (100 gm) was reacted with ethanol (300 mL) under acid catalysis (0.5 mL TFA) to produce a 95% yield of the intermediate ethyl ester 15 after refluxing for 3 hours, concentration to a solid, and recrystalization from toluene. Intermediate 15 (10 gm) was then reacted with 1.1 equivalents of oxalyl chloride in CH$_2$Cl$_2$ (200 mL) for 4 hours at room temperature to produce an 80% yield of acid chloride 16 as a crude solid after concentration at room temperature under high vacuun. Crude 16 was suspended in THF and reacted by either of the following two methods with fluoro acetate equivalents to produce compound 20.

Method A: The potassium salt (17) of ethyl fluoroacetate (3 equivalents), formed by reaction of ethyl fluoroacetate and potassium t-butoxide at 0° C. in THF, or the magnesium salt of ethyl hydrogen fluoromalonate (18) (1.5 equivalents), Me.). Each of the four sequencing premixes is defined below in Table I:

TABLE I

| | |
|---|---|
| A Premix | 60 mM Tris pH 9.0; 2.5 mM MgCl2; 4 mM Kcl; 0.04 mM DTT; 4 µMEDTA; 0.1 µM TET labeled primer; 0.66U/µL Amplitaq FS; 1.66 U/µL rTth Pyrophosphatase; 0.5 µM ddATP; 125 µM dATP; 125 µM dCTP; 150 µM c7dGTP; 125 µM dTTP. |
| C Premix | 60 mM Tris pH 9.0; 2.5 mM MgCl2; 4 mM KCl; 0.04 mM DTT; 4 µM EDTA; 0.1 µM 6-FAM labeled primer; 0.66 U/µL Amplitaq FS; 1.66 U/µL rTth Pyrophosphatase; 0.5 µM ddCTP; 125 µM dATP; 125 µM dCTP; 150 µM c7dGTP; 125 µM dTTP. |
| G Premix | 60 mM Tris pH 9.0; 2.5 mM $MgCl_2$, 4 mM Kcl; 0.04 mM DTT; 4 µM EDTA; 0.1 µM HEX labeled primer; 0.66U/µL Amplitaq FS; 1.66 U/µL rTth Pyrophosphatase; 0.375 µM ddGTP; 125 µM dATP; 125 µM dCTP; 150 µM c7dGTP; 125 µM dTTP. |
| T Premix | 60 mM Tris pH 9.0; 2.5 mM MgCl2; 4 mM Kcl; 0.04 mM DTT; 4 µM EDTA; 0.1 µM FLAN labeled primer; 0.66U/µL Amplitaq FS; 1.66 U/µL rTth Pyrophosphatase; 0.875 µM ddTTP; 125 µM dATP; 125 µM dCTP; 150 µM c7dGTP; 125 µM dTTP. | formed by reaction of isopropyl magnesium bromide (2 equivalents) and ethyl hydrogen fluoromalonate at −60° C., were added slowly to the THF suspension of 16 and allowed to react for 6 hours at 0° C. The reaction was quenched by adding 5% HCl, extracted (3 times) with EtOAc, the organic layer was dried, concentrated, and the resulting crude mixture purified by flash chromatography employing gradient elution from 6:4 hexanes/$CH_2Cl_2$ to 100% $CH_2Cl_2$ giving 35 to 50% yield of compound 20.

Method B: The phosphorous ylid 19 was slowly added to the THF suspension of 16 at −70° C., then allowed to warm to room temperature and react for 16 hours. The reaction was quenched by addition of 5% $NaHCO_3$ and stirred for 6 hours. The reaction was extracted with TBF/water (3 times) and the product was isolated as for Method A to produce intermediate 20 in >50% yield. Purified 20 intra-molecularly cyclized under base catalysis (2 equivalents NaOEt) to a cyclic intermediate 21 which decarboxylated in situ to give the 2-fluoro-1,3-dihydroxynapthalene (9a) in 50% yield. Alternatively, the cyclic intermediate 21 can be isolated in >80% yield when employing potassium t-butoxide in THF and decarboxylkated to 2-fluoro-1,3-dihydroxynapthalene (9a).

EXAMPLE 8

DNA Sequencing Employing Asymmetric Benzoxanthene Compound 2

Automated cycle sequencing was performed using a Perkin-Elmer Catalyst 800 Molecular Biology Labstation (The Perkin-Elmer Corporation, Foster City, Calif. (PE)). Four separate Sanger sequencing reactions were run employing the same -21 M13 primer labeled with 6-FAM (C terminator), TET (A terminator), HEX (G terminator), or Cl-FLAN 2 (T terminator) as described below. A mixture of the four reactions was loaded and data was generated on a Perkin-Elmer ABI Prism™ 377 DNA sequencer and associated data analysis software.

Cycle sequencing reactions were performed on the Catalyst 800 Molecular Biology Labstation using the 3.02 platform software. The Catalyst was programmed to deliver 0.6 µL of pGEM 3Z+template DNA at a concentration of 100 ng/µL, and 1.9 µL of premix defined below. Sequencing data was generated on an ABI Prisms™ 377 DNA Sequencer using a 5% Long Ranger gel (FMC corporation, Rockland, Cycle sequencing was performed on the above mixtures of template and prenixes. The cycling conditions on the Catalyst were as follows: one cycle of 96° C. for 20 seconds; 15 cycles of 94° C. for 20 seconds, 55° C. for 40 seconds, and 68° C. for 60 seconds; and 15 cycles of 94° C. for 20 seconds and 68° C. for 60 seconds.

Figure 9:
FIG. 9 shows the results of a DNA sequencing experiment employing an oligonucleotide sequencing primer labeled with a dye compound of the invention.
Figure 9:

Following thermal cycling, the four separate reactions were combined into the concentration buffer ( 83% DMSO/ 25mM EDTA/8mg/ml Blue Dextran ) and concentrated using standard Express Load methods (v 2.02 Catalyst Manual, PE). 2 mL of concentrated sample was loaded onto a well of the 377 sequencer, run, and analyzed using version 1.1 Software. The sequence between base 233 and 263 is shown in FIG. 9.

EXAMPLE 9

Microsatellite Fragments Labeled using Cl-FLAN (2), HEX and TET Labeled Primers Separated Simultaneously with ROX Labeled Internal Size Standards.

Figure 10:
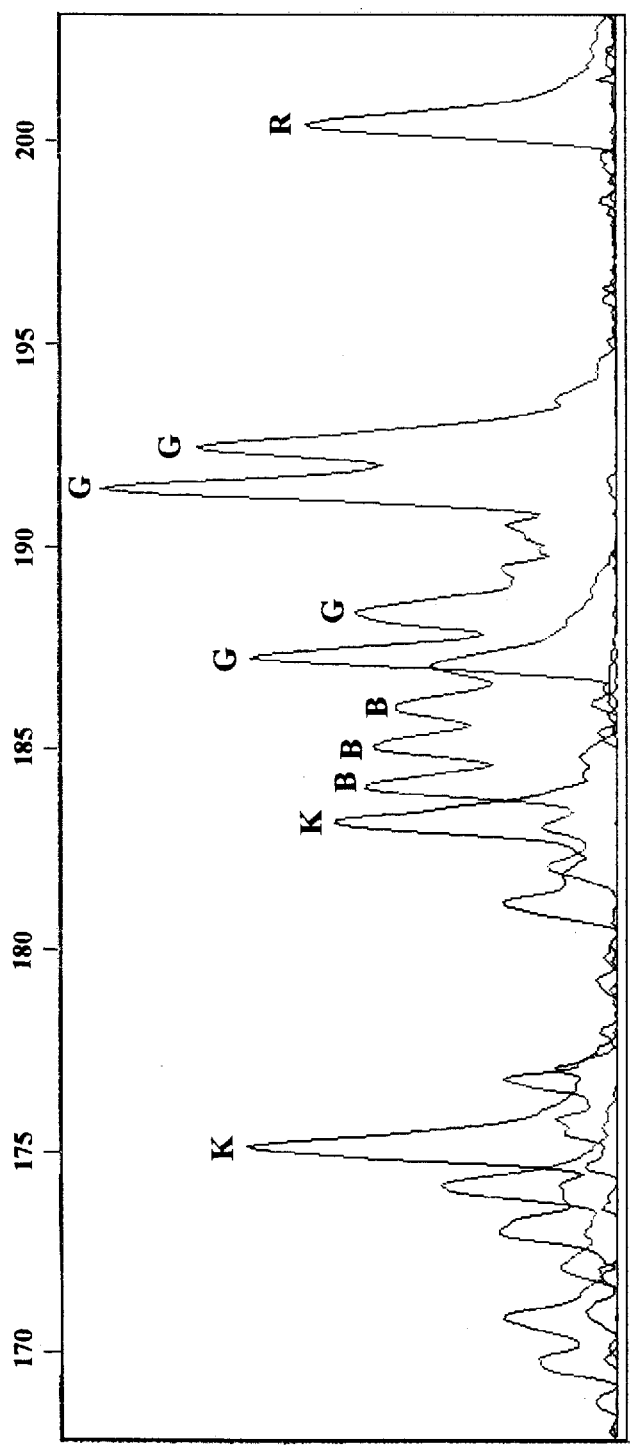
FIG. 10 shows the results of a microsatellite analysis employing an oligonucleotide PCR primer labeled with a dye compound of the invention.

PCR reactions of four loci of a human CEPH family DNA using dye labeled primers was performed as described below. The PCR products were pooled and electrophoretically separated on a Perkin-Elmer ABI Prism 377™ DNA sequencer (PE). The unique fluorescent signal of each dye labeled fragment peak was analyzed using GeneScan™ Analysis Software v 2.0.2 (PE). Referring to FIG. 10, the red peaks (labeled R) correspond to ROX (26) labeled internal standard fragments, the blue peaks (labeled B) correspond to TET labeled fragments, the green peaks (labeled G) correspond to HEX labeled fragments, and the black peaks (labeled K) correspond to Cl-FLAN (2) labeled fragments.

The PCR reactions were run on a Perkin-Elmer 9600 thernocycler (PE). A separate reaction was performed for each dye labeled primer employing the following cocktail:

| Reaction Components | Volume (µL) |
|---|---|
| Dye labeled Primer Mix (5 µM) | 1.0 |
| DNA (50 ng/µL) | 1.2 |
| 10X PE PCR Buffer II | 1.5 |
| dNTP mix (2.5 mM) | 1.5 |
| AmpliTaq[a] (5 units/µL) | 0.12 |
| 2.0 mM $MgCl_2$ | 1.2 |

-continued

| Reaction Components | Volume (μL) |
|---|---|
| Sterile D.I. Water | 8.48 |
| Total Mix | 15.0 |

The mixtures were amplified using the following cycling conditions: 1 cycle at 95° C. for 5 minutes; 10 cycles at 94° C. for 15 seconds, 55° C. for 15 seconds, and 72° C. for 30 seconds; 20 cycles at 89° C. for 15 seconds, 55° C. for 15 seconds, and 72° C. for 30 seconds; and 1 cycle at 72° C. for 10 minutes.

The amplified PCR Products were pooled by mixing the Cl-FLAN (2) and TET- labeled PCR products (0.5 μL) with 1.0 μL of each HEX labeled PCR product to give an overall ratio of mixed dye labeled fragments consisting of 1:2:1 (Cl-FLAN : HEX: TET). The pooled PCR fragments were mixed with a loading cocktail consisting of 2.5 μL formamide, 0.5 μL Blue Dextran (50 mM EDTA, 50 mg/mL Blue Dextran), and 0.5 μL Size Standard (GS-350 ROX, PE p/n 401735). The pooled mixture was denatured at 95° C. for five minutes and then loaded onto one gel lane of a PE ABI Prisms™ 377 DNA sequencer. The fragments were electrophoretically separated and detected using an acrylamide gel having the following characteristics: 0.20 mm thickness, 4.25% (wt) acrylamide, 19:1 acrylamide/bisacrylamide (wt/wt), 34-well square tooth comb, 10×TBE Buffer (89 mM Tris, 89 mM Boric Acid, 2 mM EDTA) pH of 8.3. The instrument was run using Filter Wheel A and the GS 36D-2400 Module which has the following run parameters: EP Voltage of 3000 V, EP Current of 60.0 mA, EP Power of 200 W, Gel Temperature of 51° C. and a laser power of 40 mW.

EXAMPLE 10

Comparison of the Spectral Properties, Photostability, and Chemical Stability of Rhodamine Dyes, Xanthene Dyes and the Asymmetric Xanthene Dyes of the Invention Table I below summarizes and compares various spectral and chemical properties of the asymmetric benzoxanthene dyes of the invention and other spectrally similar xanthene and rhodamine-based dyes.

TABLE II

| Dye | $\lambda_{max}$Em (nm) | Width at Half Height (nm) | Relative Photostability | Relative Brightness | Stability in $NH_4OH$-$t_{1/2}$ (hr) |
|---|---|---|---|---|---|
| HEX | 550 | 32 | 17 | 2.4 | 11 |
| (5) | 552 | 45 | 2.8 | 3.9 | 430 |
| (6) | 554 | 47 | — | — | — |
| (4) | 564 | 41 | — | — | — |
| (1) | 565 | 45 | 5.3 | 1.6 | 478 |
| (2)CL-FLAN | 568 | 42 | 5.1 | 2.1 | 146 |
| (7) | 570 | 45 | 1.1 | 1.6 | — |
| (8) | 572 | 47 | — | — | — |
| TAMRA | 577 | 39 | — | 0.9 | 1.3 |
| NAN | 579 | 44 | 0.3 | 1 | 52 |
| (3) | 583 | 43 | 1.7 | 1.1 | 14 |
| ROX | 594 | 53 | — | 0.5 | 272 |
| DEB | 598 | 48 | 0.3 | 0.3 | — |

Figure 2B:
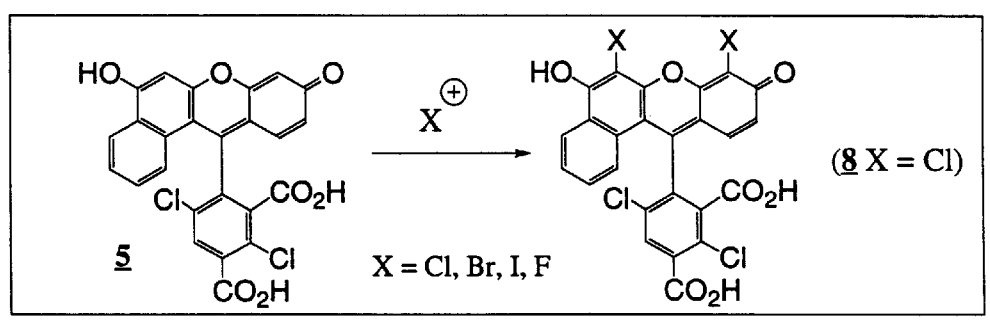

See FIGS. 1 and 2 for the structures of the dyes referred to in the table. All data are reported for pure dye isomer 2.

All emission spectra were recorded in 1×TBE buffer at pH 8.4 in dye solutions having an absorbance of 0.05 at $\lambda_{max}$Abs (ca. $1\times10^{-6}$ M) at room temperature. Photodecomposition rate was determined for equal volumes of the dyes at initially 1 absorption unit at $\lambda_{max}$Abs and run in pairs at equal volumes under equal high intensity white light irradiation at 35° C. in 1×TBE buffer pH 8.4. Absorption spectra of aliquots were taken at 1 hour intervals and the intensities at $\lambda_{max}$Em were fitted with first order exponential curves to determine the $t_{1/2}$ rate for loss of dye. Relative brightness at $\lambda_{max}$Em was determined using 514 nm excitation of dyes at approximately equal concentrations. ($\lambda_{max}$Abs=0.05). For the $NH_4OH$ stability measurements the dyes were diluted in concentrated ammonia hydroxide at approximately equal concentrations ($\lambda_{max}$Abs =1) and incubated at 60° C. for 20 hours in sealed vials. Absorption spectra of aliquots were taken at 1 hour intervals and the intensities at $\lambda_{max}$Em were fitted with first order exponential curves to determine the $t_{1/2}$ for dye decomposition.

All publications and patent applications are herein incorporated by reference to the same extent as if each individual publication or patent application was specifically and individually indicated to be incorporated by reference.

Those having ordinary skill in the chemical and biochemical arts will clearly understand that many modifications are possible in the preferred embodiment without departing from the teachings thereof. All such modifications are intended to be encompassed within the following claims.

We claim:

1. A compound having the formula:

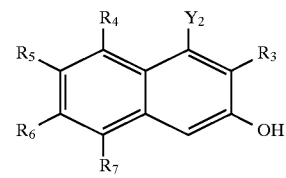

wherein:

$R_3$ is selected from the group consisting of fluorine, chlorine, sulfonate, amino, amido, nitrite, lower alkoxy, and linking group;

$R_4$–$R_7$ taken separately are selected from the group consisting of hydrogen, fluorine, chlorine, lower alkyl, lower alkene, lower alkyne, sulfonate, amino, amido, nitrile, lower alkoxy, and linking group; and $Y_2$ is selected from the group consisting of hydroxyl and amine.

2. The compound of claim 1 wherein $R_3$ is fluorine.
3. The compound of claim 1 wherein $Y_2$ is hydroxyl.
4. The compound of claim 1 wherein $R_3$ is chlorine.
5. The compound of claim 1 wherein $Y_2$ is amine.

* * * * *

UNITED STATES PATENT AND TRADEMARK OFFICE
CERTIFICATE OF CORRECTION

PATENT NO. : 5,840,999
DATED : Nov. 24, 1998
INVENTOR(S) : Benson et al.

It is certified that error appears in the above—identified patent and that said Letters Patent is hereby corrected as shown below:

Col. 28, line 50, "nitrite" should be "nitrile".

Col. 2, line 67, "lower allyl" should be "lower alkyl".

Col. 3, line 1, "ammonium" should be "imminium".

Col. 7, line 45, "inmminiurn" should be "imminium".

Col. 7, line 46, "rhodamnine" should be "rhodamine".

Col. 7, line 62, "lower allkyl" should be "lower alkyl" and "lower allyne" should be "lower alkyl".

Col. 11, line 48, "uracii" should be "uracil".

Signed and Sealed this

Seventh Day of September, 1999

Attest:

Q. TODD DICKINSON

Attesting Officer

Acting Commissioner of Patents and Trademarks